US009198981B2

(12) United States Patent
Ambati et al.

(10) Patent No.: US 9,198,981 B2
(45) Date of Patent: Dec. 1, 2015

(54) MODULATION OF ANGIOGENESIS

(75) Inventors: Balamurali Krishna Ambati, Salt Lake City, UT (US); Jayakrishna Ambati, Lexington, KY (US); Nirbhai Singh, Salt Lake City, UT (US)

(73) Assignee: The University of Kentucky, Lexington, KY (US)

( * ) Notice: Subject to any disclaimer, the term of this patent is extended or adjusted under 35 U.S.C. 154(b) by 1126 days.

(21) Appl. No.: 11/582,662

(22) Filed: Oct. 17, 2006

(65) Prior Publication Data

US 2007/0191273 A1 Aug. 16, 2007

Related U.S. Application Data

(60) Provisional application No. 60/764,269, filed on Feb. 1, 2006.

(51) Int. Cl.
*C12N 15/11* (2006.01)
*A61K 48/00* (2006.01)
*C07H 21/02* (2006.01)
*C07H 21/04* (2006.01)
*A61K 38/17* (2006.01)
*C12N 15/113* (2010.01)

(52) U.S. Cl.
CPC ............ *A61K 48/005* (2013.01); *A61K 38/177* (2013.01); *C12N 15/1138* (2013.01); *C12N 2310/14* (2013.01); *C12N 2310/53* (2013.01)

(58) Field of Classification Search
USPC ........... 435/6, 91.1, 325, 375; 536/23.1, 24.3, 536/24.33, 24.5; 514/44
See application file for complete search history.

(56) References Cited

U.S. PATENT DOCUMENTS

| 5,861,484 | A | 1/1999 | Kendall |
| 6,011,003 | A | 1/2000 | Charnock-Jones |
| 6,773,916 | B1 * | 8/2004 | Thiel et al. .................... 435/326 |
| 2005/0222066 | A1 | 10/2005 | Richards |
| 2005/0233998 | A1 | 10/2005 | Jadhav |

OTHER PUBLICATIONS

Fritsch et al. Conditional gene knock-down by CRE-dependent short interfering RNAs. EMBO Reports, 2004 vol. 5:178-182.*
Ambati et al. (Nature, vol. 443, Oct. 26, 2006, pp. 993-997).*
See Shen et al. (Gene Therapy, 2006 vol. 13, pp. 225-234, published online Sep. 29, 2005).*
Luttun et al. (Nature Medicine, 2000 vol. 8:831-840).*
Bumseok, Kim; Q. Tang; P. S. Biswas; J. Xu; R. M. Schiffelers; F.Y. Xie; A. S. Ansari; P. V. Scaria; M. C. Woodie; P. Lu; and B. T. Rouse "Inhibition of Ocular Angiogenesis by siRNA Targeting Vascular Endothelial Growth Factor Pathway Genes" American Journal of Pathology, vol. 165, No. 6, Dec. 2004.
Shen, J.; R. Samul; R. L. Silva; H. Akiyama; H. Liu; Y. Saishin; S. F. Hackett; K. Fosnaugh; C. Vargeese; A. Gomez; K. Bouhana; R. Aitchison; and P. Pavco "Suppresion of Ocular Neovascularization with siRNA targeting VEGF receptor 1" Gene Therapy (2005) pp. 1-10.

* cited by examiner

*Primary Examiner* — Terra C Gibbs
(74) *Attorney, Agent, or Firm* — Crowell & Moring LLP

(57) ABSTRACT

This invention relates to compounds, compositions, and methods for the treatment of traits, diseases and conditions that respond to the modulation of angiogenic growth factor bioavailability or biological activity.

13 Claims, 6 Drawing Sheets
(4 of 6 Drawing Sheet(s) Filed in Color)

SEQUENCE LISTING

<160> NUMBER OF SEQ ID NOS: 15

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aaacaaccac aaaauacaac a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aatgattgta ccacacaaag t                                              21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tctcggatct ccaaattta                                                 19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaggctgtt ttctctcgga t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaagcacaa ggaatgattg t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaggccatt ttctctcgga t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaagcagga ggaatgattg t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
aatgattgta ccacacaaag t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacgactgca caactcagag c                                              21

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggtgagcac tgcggca                                                   17

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgagtcctt taatgtttga c                                              21

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Asp Cys Thr Thr Gln Ser
  1               5

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aaugauugua ccacacaaag u                                              21

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
ucucggaucu ccaaauuua                                                    19

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 15

His His His His His His
 1               5
```

MODULATION OF ANGIOGENESIS

CROSS REFERENCE TO RELATED APPLICATIONS

This application claims priority to U.S. Provisional Application Ser. No. 60/764,269 filed Feb. 1, 2006, the disclosure of which is incorporated herein by reference.

TECHNICAL FIELD

This invention relates to compounds, compositions, and methods for the treatment of traits, diseases and conditions that respond to the modulation of angiogenic growth factor bioavailability or biological activity.

BACKGROUND

The formation of new blood vessels either from differentiating endothelial cells during embryonic development (vasculogenesis) or from pre-existing vessels during adult life (angiogenesis) is an essential feature of organ development, reproduction, and wound healing in higher organisms. Angiogenesis is also necessary for certain pathological processes including tumorigenesis and retinopathy. While several growth factors can stimulate angiogenesis vascular endothelial growth factor (VEGF) is a potent angiogenic factor that acts via the endothelial cell-specific receptor tyrosine kinases fms-like tyrosine kinase (Flt1) and fetal liver kinase (Flk1) (also designated KDR). These two VEGF receptors and a third orphan receptor, Flt4 constitute a subfamily of class III receptor tyrosine kinases that contain seven extracellular immunoglobulin-like domains and a split intracellular tyrosine kinase domain. These three receptors have 31-36% amino acid identity in their extracellular ligand-binding domains.

VEGF is a homodimeric, cysteine-rich protein that can occur in at least four forms due to alternative splicing of its mRNA. VEGF is a high-affinity ligand for Flt1 and Flk1. A closely related member of the VEGF family is placental growth factor (PlGF), which has 47% amino acid identity with VEGF. PlGF also occurs in two alternatively spliced forms which differ in the presence or absence of a basic heparin binding domain of 21 amino acids.

Various natural and synthetic mechanisms exist for modulating growth factor activity including those that regulate the availability of agents that interact with growth factors in situ and in vivo. Accordingly, additional compounds, compositions and methods for regulating growth factor-agent interactions are desirable.

SUMMARY

Provided herein are compounds, compositions and methods for modulating angiogenesis in a target tissue. More specifically, provided herein are compounds, compositions and methods for modulating the bioavailability and activity of growth factors such as VEGF and/or PlGF. Such compounds, compositions and methods effectively modulate growth factor activity by regulating growth factor interactions with growth factor inactivating agents. Such agents generally regulate growth factor activity by sequestering the growth factor in a complex that inhibits growth factor growth-promoting activities. Also provided are methods for identifying compounds that modulate growth factor sequestration.

Accordingly, in various embodiments, methods of treating or preventing a condition associated with decreased vascularity in a subject are provided. The methods include administering to the subject a compound that regulates the bioavailability or biological activity of VEGF or PlGF by modulating the availability of a VEGF or PLGF inactivating agent. The administering is sufficient to treat or prevent the condition in the subject.

The inactivating agent generally forms a complex with VEGF or PlGF by binding to VEGF or PlGF. A compound provided herein can modulate VEGF or PlGF bioavailability or biological activity by preventing, inhibiting or disrupting the formation of the complex. In one aspect, this is accomplished by decreasing the amount of the agent, such as by regulating the expression of the agent. In other aspects, preventing, inhibiting or disrupting the formation of the complex includes binding of the compound with complexed or uncomplexed inactivating agent. VEGF includes VEGF-A, VEGF-B, VEGF-C and VEGF-D and PlGF includes PlGF-1 or PlGF-2.

In one aspect, the agent comprises a VEGFR1, VEGFR2 or VEGFR3 polypeptide. Exemplary VEGFR1 polypeptides are encoded by the fms-like tyrosine kinase (Flt-1) gene. Exemplary polypeptides include isoforms such as sflt-1 and mbflt-1.

Conditions associated with decreased vascularity include ocular disorders, preeclampsia, cerebrovascular disorders, cardiovascular disorders, systemic hypertension, peripheral vascular disease, vascular regeneration/recovery, and wound healing disorders.

In one embodiment, the compound comprises a double stranded nucleic acid molecule having one strand that is at least 95% complementary to at least a portion of a nucleic acid sequence encoding the agent. In one aspect, the nucleic acid molecule comprises an interfering RNA molecule selected from shRNA, siRNA and miRNA. The length of the interfering RNA can be 10 to 80, 10 to 70, 10 to 60, 10 to 50, 10 to 40, or 10 to 30 nucleotides in length.

In another embodiment, the compound includes a purified antibody or antigen-binding fragment that specifically binds the agent.

In yet another embodiment, the expression of the agent is regulated by an inducible excision system. In one aspect, the inducible excision system is cre-lox or FLP/FRT excision system. In general, excision is facilitated by the introduction of exogenous CRE recombinase.

In some aspects, the compound is administered via a topical, intravitreal, transcleral, periocular, conjunctival, sub-tenon, intracameral, subretinal, subconjunctival, retrobulbar, suprachoriodal, intravenous, oral or intracanalicular route. In other aspects, the compound is included in a composition, such as a pharmaceutically acceptable composition, which facilitates administration of the compound to a subject.

In another embodiment, a short interfering nucleic acid (siNA) molecule that promotes VEGF bioavailability by down-regulating the expression of a polypeptide encoded by the fms-like tyrosine kinase (Flt-1) gene. Exemplary polypeptides include isoforms such as sflt-1 and mbflt-1.

In one aspect, the siNA molecule includes a sense region and an antisense region. The antisense region includes a sequence complementary to a sequence encoded by the fms-like tyrosine kinase (Flt-1) gene and the sense region includes a sequence complementary to the antisense region. A siNA molecule is assembled from two nucleic acid fragments—one fragment includes the sense region and the second fragment includes the antisense region of the siNA molecule. In some aspects, the sense region and the antisense region are covalently connected via a linker molecule, such as a polynucleotide linker or a non-nucleotide linker.

In another aspect, the siNA molecule is RNA, such as shRNA, siRNA and/or miRNA. In various other aspects, the siNA molecule includes a sequence selected from: a) a sequence comprising any one of SEQ ID NOs.:1, 2, 3, 4, 5, 6, or 7, and having a length of 21 to 50 nucleotides; b) a sequence consisting of any one of SEQ ID NOs.:1, 2, 3, 4, 5, 6, or 7; or c) a sequence comprising a region of at least 19 contiguous nucleotides having at least 90% sequence complementarity to, or at least 90% sequence identity with, any one of SEQ ID NO:1, 2, 3, 4, 5, 6, or 7, and having a length of 21 to 50 nucleotides. In another aspect, a cell including a siNA molecule of the invention is provided.

In another embodiment, a vector that includes a nucleic acid sequence encoding at least one siNA molecule of the invention in a manner that allows expression of the nucleic acid molecule is provided. In one aspect, the vector is included in a cell, such as a mammalian cell.

In another embodiment, a siNA molecule of the invention is linked to cell-penetrating peptide such as penetratin, transportan, pIsl, TAT, pVEC, MTS, and MAP. In one aspect, the cell penetrating peptide is linked to the 5' end of the siNA molecule by a covalent bond.

In other embodiments, siRNA molecules provided herein are included in a composition, such as a pharmaceutically acceptable carrier.

In yet another embodiment, a method of identifying a compound that regulates the bioavailability or biological activity of VEGF in vivo or in situ, is provide. The method includes a) contacting corneal tissue with a test compound that regulates, or is believed to regulate: i) the expression of a VEGF inactivating agent; or ii) the ability of the VEGF inactivating agent to bind to VEGF; b) measuring the bioavailability or biological activity of VEGF; and c) identifying a compound that regulates the bioavailability or biological activity of VEGF.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

This patent or application file contains at least one drawing executed in color. Copies of this patent or patent application publication with color drawing(s) will be provided by the Office upon request and payment of the necessary fee.

FIG. 1, panel B depicts a non-reducing western blot of mouse cornea revealing immunoreactive bands of VEGF-A at 100-130 kDa corresponding to bound forms and negligible immunoreactivity at 45-50 kDa corresponding to the free form.

FIG. 1, panel C depicts sflt-1 (lane 1) and VEGF-A (lane 3) transcripts in mouse cornea identified by representative RT-PCR. Lane 2 is water (template negative) control.

FIG. 1, panel D and panel E depict sflt-1 mRNA detected by in situ hybridization in mouse corneal epithelium (epi) and stroma (str). Antisense RNA probes show purple-brown reactivity. Sense RNA probes show negligible reactivity.

FIG. 1, panel F depicts immunolocalization (brown) of sflt-1 protein in mouse cornea.

FIG. 1, panel G depicts reducing western blots using an antibody against the amino (N)-terminus of flt-1 that recognizes both mbflt-1 and sflt-1 and an antibody against the unique carboxyl terminus of sflt-1 specific antibody reveal that mouse cornea (1) contains primarily sflt-1 (60 kDa) while conjunctiva (2) contains primarily mbflt-1 (190 kDa).

FIG. 1, panel H depicts western blot analysis of two independent mouse cornea samples immunoprecipitated with anti-VEGF-A antibody and immunoblotted with a biotinylated antibody against the amino (N)-terminus of flt-1 that recognizes both mbflt-1 and sflt-1 reveals that VEGF-A interacts with sflt-1 (60 kDa). Subsequent immunoblot with a biotinylated anti-VEGF-A antibody confirms the pull-down of VEGF-A by the immunoprecipitating antibody.

FIG. 2, panel B shows that NLS-β-galactosidase expression fails to induce Cre expression (brown) in cornea within 1 hour of eye drop application as demonstrated by immunolocalization in cell nuclei stained red.

FIG. 2, panel C depicts a reducing western blot of Cre expression.

FIG. 2, panel D depicts Xgal staining of corneal flat mount of ROSA26R lacZ reporter mouse confirms expression of β-galactosidase (blue) 2 days after Cre expression.

FIG. 2, panel E depicts representative corneal flat mounts showing CD31$^+$ (green) LYVE-1$^-$ blood vessels in flt-1$^{loxP/loxP}$ mouse corneas 14 days after treatment with NLS-Cre eye drops.

FIG. 2, panel F depicts representative corneal flat mounts showing CD31$^+$ (green) LYVE-1 blood vessels in flt-1$^{loxP/loxP}$ mouse corneas 14 days after treatment with NLS-β-galactosidase expression.

FIG. 2, panel G depicts the absence of corneal vascularization in wild-type mice after topical application of NLS-Cre.

FIG. 2, panel H depicts the absence of corneal vascularization in wild-type mice after topical application of NLS-β-galactosidase.

FIG. 2, panel I depicts a western blot indicating that topical application of NLS-Cre leads to Cre expression in the mouse cornea and is enhanced by the prior topical application of proparacaine eye drops (+P) compared to no prior application (−P).

FIG. 3, panel B is a bar graph depicting data generated from an ELISA. The data indicates that sflt-1 protein is reduced in wild-type mouse corneas 3 days after injection of pshRNA-sflt-1 but not pshRNA-mbflt-1. * $P<0.05$, Bonferroni corrected Mann Whitney U test. Error bars depict s.e.m.

FIG. 3, panel C is a bar graph depicting data generated from an ELISA. The data indicates that free VEGF-A protein is increased in wild-type mouse corneas 3 days after injection of pshRNA-sflt-1 but not pshRNA-mbflt-1. * $P<0.05$, Bonferroni corrected Mann Whitney U test. Error bars depict s.e.m.

FIG. 3, panel D provides an image of an eye expressing pshRNA-sflt-1.

FIG. 3, panel E depicts a corneal flat mount showing CD31$^+$ (green) LYVE-1$^-$ blood vessels at 14 days after injection. pshRNA-sflt-1 expression induces CV in wild-type mice. Scale bars are 500 μm.

FIG. 3, panel F depicts a corneal flat mount showing CD31$^+$ (green) LYVE-1$^-$ blood vessels at 14 days after injection. pshRNA-mbflt-1 expression fails to induce CV in wild-type mice. Scale bars are 500 μm.

FIG. 3, panel G is a graph depicting a decrease in sflt-1 (sVEGFR1) expression by a siRNA sequence that targets sflt-1 (sVEGFR1).

FIG. 3, panel H depicts suppression of unique tail of sFLT by siRNA targeting unique tail.

FIG. 3, panel I depicts suppression of mRNA of VEGF binding domains (553 bp) of sFLT by siRNA targeting unique tail, while 18sRNA (315 bp) is unaffected.

FIG. 3, panel J depicts western blot analysis of VEGF expression (band visible at 25 kD) in mouse corneas using immunoprecipitation by antibody to sFLT unique tail and demonstrating that siRNA knock down of sflt-1 expression frees VEGF from sflt-1 sequestration.

FIG. 4, panel B is a bar graph showing that sflt-1/Fc administration inhibits CV in corn1 and Pax6$^{+/-}$ mice compared to IgG1/Fc (by 87±2% in corn1; P=0.01; by 85±3% in Pax6$^{+/-}$; P=0.03) and to control untreated mice (by 87±2% in corn1; P=0.01; by 84±3% in Pax6$^{+/-}$; P=0.03). Significance by Bonferroni corrected Mann Whitney U test. Error bars depict s.e.m.

FIG. 4, panel C depicts flat mounts showing CD31$^+$ (green) LYVE-1—corneal blood vessels.

FIG. 4, panel D depicts immunostaining of a cornea and revealing a deficiency of sflt-1 (brown) in cornea with aniridia-associated vascularization (top), revealed by vascular cell adhesion molecule-1 (VCAM-1) staining (red) compared to the avascular cornea (lack of VCAM-1 staining) of a different cornea without aniridia (bottom).

FIG. 4, panel E depicts a marked deficiency of sflt-1 (reddish brown) staining in cornea of Antillean manatee.

FIG. 4, panel F depicts the presence of sflt-1 (reddish brown) staining in cornea of a dugong.

FIG. 4, panel G depicts the presence of sflt-1 (reddish brown) staining in cornea of an African elephant.

FIG. 4, panel H depicts the presence of sflt-1 (reddish brown) staining in cornea of a beaked whale.

FIG. 4, panel I depicts reducing western blots using an antibody against the amino (N) terminus of flt-1 reveal presence of sflt-1 (60 kDa) and absence of mbflt-1 (190 kDa) in corneas of bottlenose dolphin (1) and Asian elephant (2). Scale bars are 200 μm.

Like reference symbols in the various drawings indicate like elements.

DETAILED DESCRIPTION

Figure 1:
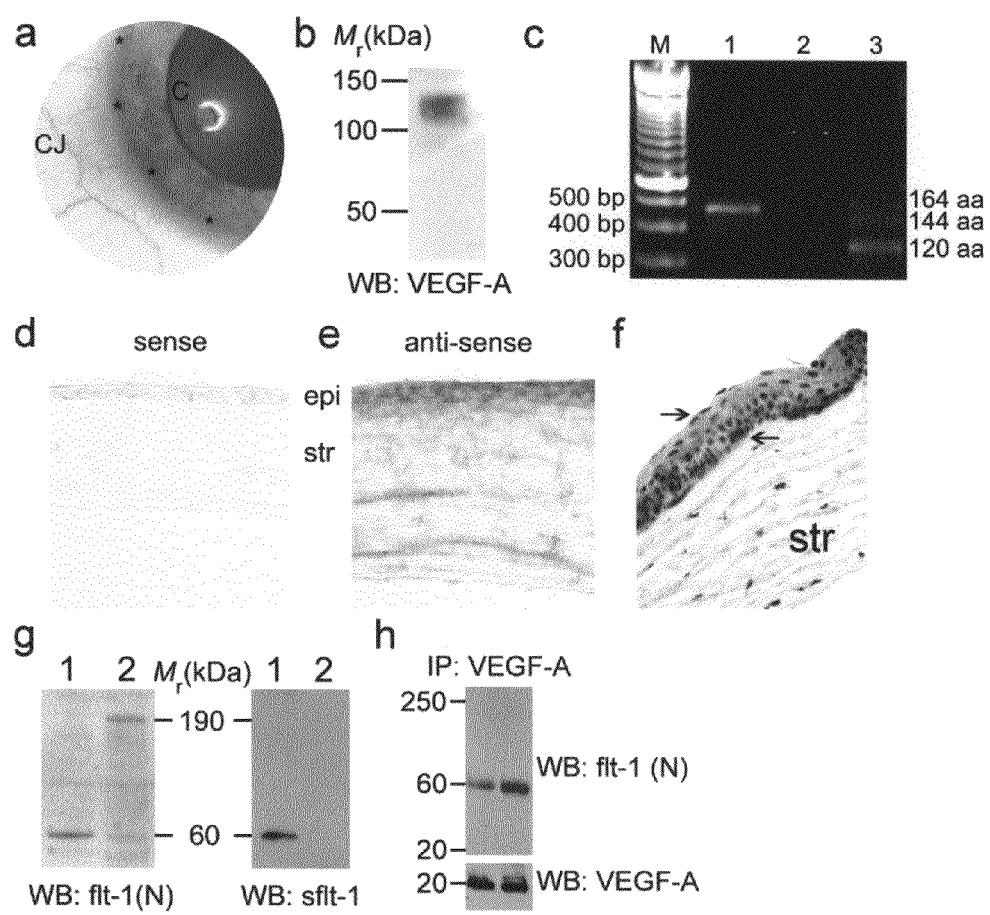
FIG. 1, panel A is a photo of a human eye demonstrating abrupt termination of blood vessels in the conjunctiva (CJ) at its border with the cornea (C), the limbus (*).

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

As will be described in more detail below, the invention is based, at least in part, on compounds, compositions and methods for regulating angiogenesis in a target tissue. More specifically, provided herein are compounds, compositions and methods for modulating the bioavailability and activity of VEGF or PlGF. Such compounds, compositions and methods effectively modulate VEGF or PlGF activity by regulating VEGF or PlGF interactions with VEGF or PlGF inactivating agents. Such agents generally regulate VEGF or PlGF activity by sequestering VEGF or PlGF in a complex that inhibits VEGF or PlGF vascularization-promoting activities.

Accordingly, in various embodiments, methods of treating or preventing a condition associated with decreased vascularity in a subject, are provided. The methods include administering to the subject a compound that regulates the bioavailability or biological activity of VEGF or PlGF by modulating the availability of a VEGF or PLGF inactivating agent. The administering is sufficient to treat or prevent the condition in the subject. An inactivating agent, as described herein, can form a complex with VEGF or PlGF by binding to VEGF or PlGF. A compound provided herein can modulate VEGF or PlGF bioavailability or biological activity by preventing, inhibiting or disrupting the formation of the complex. In one aspect, this is accomplished by decreasing the amount of the agent, such as by reducing or inhibiting the expression of the agent. By "reduce or inhibit" is meant the ability to cause an overall decrease of 20% or greater, more preferably of 40%, 50%, 60%, 70%, 80%, and 90% or greater change in the level of the agent. By "expression" is meant the detection of a gene or polypeptide by standard art known methods. For example, polypeptide expression is often detected by western blotting, DNA expression is often detected by Southern blotting or polymerase chain reaction (PCR), and RNA expression is often detected by northern blotting, PCR, or RNAse protection assays.

By "gene", or "target gene" or "target DNA", is meant a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of FRNA or ncRNA involved in functional or regulatory cellular processes. Abberant fRNA or ncRNA activity leading to disease can therefore be modulated by siNA molecules of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.).

By "compound" is meant any small molecule chemical compound, antibody, nucleic acid molecule, or polypeptide, or fragments thereof. Compounds particularly useful for the compositions and methods of the invention can alter, preferably increase, the bioavailability or biological activity of VEGF or PlGF by at least 10%, 20%, 30%, 40%, 50%, 60%, 70%, 80%, 90% or more. Accordingly, the compounds, compositions and methods provided herein can be used to treat conditions associated with decreased vascularity. For example, tissue that requires vascularization, neovascularization and/or revascularization of in a subject can be treated by a compound, composition or method provided herein. Such conditions are described in more detail below and include ocular disorders, preeclampsia, cerebrovascular disorders, cardiovascular disorders, and wound healing disorders, or any proliferative, inflammatory or neurologic disorder that can be successfully treated or prevented by increasing the bioavailability or biological activity of a growth factor.

Accordingly, in one embodiment, compounds provided herein include nucleobase oligomers that regulate the expression of a target nucleic acid sequence encoding an inactivating agent. By "nucleobase oligomer" is meant an oligomer, regardless of length, that is complementary to the coding strand or mRNA of any nucleic acid sequence encoding an inactivating agent. A nucleobase oligomer generally includes a chain of at least eight, twelve, or at least sixteen nucleobases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. patent Publication Nos. 20030114412 (see for example paragraphs 27-45 of the publication) and 20030114407 (see for example paragraphs 35-52 of the publication), incorporated herein by reference. The nucleobase oligomer can also be targeted to the translational start and stop sites.

The term "nucleobase oligomer" includes short interfering nucleic acid (siNA) molecules such as dsRNA, siRNA, shRNA, miRNA or mimetics thereof that inhibits the expression of a target gene (see below). An inhibitory nucleobase oligomer typically reduces the amount of a target mRNA, or protein encoded by such mRNA, by at least 5%, more desirable by at least 10%, 25%, 50%, or even by 75%, 85%, or 90% relative to an untreated control. Methods for measuring both mRNA and protein levels are well-known in the art; exemplary methods are described herein. The nucleobase oligomer (or a portion thereof) may contain a modified backbone. Phosphorothioate, phosphorodithioate, and other modified backbones are known in the art. The nucleobase oligomer may also contain one or more non-natural linkages.

Specific examples of some modified nucleic acids or nucleobases envisioned for this invention may contain phosphorothioates, phosphotriesters, methyl phosphonates, short chain alkyl or cycloalkyl intersugar linkages or short chain heteroatomic or heterocyclic intersugar linkages. In other embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497 (1991)). Other preferred oligonucleotides may contain alkyl and halogen-substituted sugar moieties. Oligonucleotides may also have sugar mimetics such as cyclobutyls in place of the pentofuranosyl group. Other embodiments may include at least one modified base form. Some specific examples of such modified bases include 2-(amino)adenine, 2-(methylamino) adenine, 2-(imidazolylalkyl)adenine, 2-(aminoalklyamino) adenine, or other heterosubstituted alkyladenines. Each of the above is referred to as a "modification" herein.

As previously noted, a nucleobase oligomer includes small nucleic acid molecules useful for RNA interference (RNAi), such as short interfering nucleic acid (siNA), short interfering RNA (siRNA), double-stranded RNA (dsRNA), micro-RNA (miRNA), and short hairpin RNA (shRNA) molecules capable of mediating or that mediate RNA interference (RNAi) against the expression of VEGF or PlGF inactivating agents, such as polypeptide encoded by the fms-like tyrosine kinase (Flt-1) gene. Such small nucleic acid molecules are useful, for example, in providing compositions for treatment of traits, diseases and conditions that can respond to modulation of VEGF or PlGF activity in a subject or organism. Such proliferative diseases and conditions include ocular diseases and conditions, dermatological diseases and conditions, and any other disease, condition, trait or indication that can respond to the level of VEGF activity in a cell or tissue.

Accordingly, nucleobase oligomers provided herein include short interfering nucleic acid (siNA) molecules. The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating expression of an inactivating agent by mediating RNA interference "RNAi" or gene silencing in a sequence-specific manner. For example the siNA can be a double-stranded nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof). Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate, or 5',3'-diphosphate.

In some embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. Short hairpin interfering RNA (shRNA) is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Each sequence of a siNA molecule of the invention is independently about 15 to about 30 nucleotides in length, in specific embodiments about 15, 16, 17, 18, 19, 20, 21, 22, 23, 24, 25, 26, 27, 28, 29, or 30 nucleotides in length. In another embodiment, the siNA duplexes of the invention independently comprise about 15 to about 30 base pairs (e.g., about 15, 16, 17, 18, 19, 20, 21, 22, 23, 24, 25, 26, 27, 28, 29, or 30). One or more strands of the siNA molecule of the invention independently comprises about 15 to about 30 nucleotides (e.g., about 15, 16, 17, 18, 19, 20, 21, 22, 23, 24, 25, 26, 27, 28, 29, or 30) that are complementary to a target nucleic acid molecule. siNA molecules of the invention comprising hairpin or circular structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 15 to about 25 (e.g., about 15, 16, 17, 18, 19, 20, 21, 22, 23, 24, or 25) base pairs.

siNA molecules provided herein include those that having a sequence of any one of SEQ ID NOs.:1, 2, 3, 4, 5, 6, or 7. Such molecules include those that consist of any one of SEQ ID NOs.:1, 2, 3, 4, 5, 6, or 7. In addition, siNA molecules provided herein include those having a region of at least 19 contiguous nucleotides having at least 90% sequence complementarity to, or at least 90% sequence identity with, any one of SEQ ID NO:1, 2, 3, 4, 5, 6, or 7. "Sequence identity" herein means the extent to which two nucleotide sequences are invariant. "Sequence alignment" means the process of lining up two or more sequences to achieve maximal levels of identity for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity.

By "RNA interference" or "RNAi" is meant a biological process of inhibiting or down regulating gene expression in a cell as is generally known in the art and which is mediated by short interfering nucleic acid molecules, see for example Zamore and Haley, Science, 309:1519; Vaughn and Martienssen, Science, 309:1525; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914). In addition, as used herein, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at both the post-transcriptional level or the pre-transcriptional level. In a non-limiting example, epigenetic modulation of gene expression by siNA molecules of the invention can result from siNA mediated modification of chromatin structure or methylation patterns to alter gene expression. In another non-limiting example, modulation of gene expression by siNA molecules of the invention can result from siNA mediated cleavage of RNA (either coding or non-coding RNA) via RISC, or alternately, translational inhibition as is known in the art. In another embodiment, modulation of gene expression by siNA molecules of the invention can result from transcriptional inhibition (see for example Janowski et al., 2005, Nature Chemical Biology, 1:216).

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

Interfering RNA of embodiments of the invention appear to act in a catalytic manner for cleavage of target mRNA, i.e., interfering RNA is able to effect inhibition of inactivating agent expression in substoichiometric amounts. As compared to antisense therapies, significantly less interfering RNA is required to provide a therapeutic effect under such cleavage conditions. siNA molecules of the invention include duplex forming oligonucleotides "DFOs", (see for example Vaish et al., U.S. Ser. No. 10/727,780 filed Dec. 3, 2003 and International PCT Application No. US04/16390, filed May 24, 2004).

In some embodiments, an siNA molecule provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

Penetratin is a 16-amino-acid polypeptide derived from the third alpha-helix of the homeodomain of Drosophila antennapedia. Its structure and function have been well studied and characterized: Derossi et al., Trends Cell Biol., 8:84-87, 1998; Dunican et al., Biopolymers, 60:45-60, 2001; Hallbrink et al., Biochim. Biophys. Acta, 1515:101-09, 2001; Bolton et al., Eur. J. Neurosci., 12:2847-55, 2000; Kilk et al., Bioconjug. Chem., 12:911-16, 2001; Bellet-Amalric et al., Biochim. Biophys. Acta, 1467:131-43, 2000; Fischer et al., J. Pept. Res., 55: 163-72, 2000; Thoren et al., FEBS Lett., 482:265-68, 2000.

As previously noted, a compound provided herein modulates the ability of an inactivating agent to form a complex with VEGF or PlGF by binding to VEGF or PlGF. An "inactivating agent," as used herein includes any polypeptide encoded by the fms-like tyrosine kinase (Flt-1) gene. Exemplary polypeptides include isoforms such as sflt-1 and mbflt-1.

In another embodiment, a compound provided herein includes antibodies that prevent, inhibit or disrupt the formation of a growth factor-inactivating agent complex by specifically binding to the inactivating agent. Such neutralizing antibodies include polyclonal as well as monoclonal antibodies. The production and identification of antibodies that bind to a target molecule is well known in the art. By "specifically binds" is meant a compound or antibody which recognizes and binds the inactivating agent but that does not substantially recognize and bind other molecules in a sample, for example, a biological sample, which naturally includes a polypeptide of the invention.

Also included are humanized antibodies. By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', F(ab').sub.2, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarily determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95% of the humanized antibody residues will correspond to those of the parental FR and CDR sequences.

In yet another embodiment, a compound of the invention includes compounds that facilitate the ablation of a genetic sequence encoding an inactivating agent. Such compounds include Cre recombinase (e.g., NLS-Cre) which can be used in methods of achieving on-demand cre-lox recombination for gene deletion. The data provided herein indicate that NLS-Cre can be injected into various different compartments of the eye to achieve spatial targeting of any gene. Further, the present studies demonstrate that application of topical eye drops of NLS-Cre lead to Cre-expression and recombination and gene deletion of "floxed" genes in the cornea. Accordingly, methods of conditionally reducing the expression of a coding sequence in a target cell are provided. The term "conditionally reduced expression" refers to the flexibility inherent in the methods/vectors of this invention, which enable regulation of reducing expression of a coding sequence in a target cell. In one embodiment, reducing expression via the vectors/methods of this invention is controlled over time, or in a cell or tissue-specific manner.

The cre recombinase is derived from a P1 bacteriophage (Abremski and Hoess, J. Biol. Chem. 259:1509, 1984) which acts on a specific 34 base pair DNA sequence known as "loxP" (locus of crossover), which is, in turn, comprised of two 13 base pair inverted repeats (serving as the recombinase binding sites) flanking an 8 base pair core sequence (Current Opinion in Biotechnology 5:521, 1994). Cre catalyzes the rearrangement of DNA sequences that contain loxP sites. Recombination between two loxP sites (catalyzed by the cre protein) causes, in certain cases, the loss of sequences flanked by these sites (for a review see N. Kilby et al, Trends Genet., 9:413, 1993). Compounds, compositions and methods provided herein encompass the introduction of Cre recombinase in to a cell or tissue in order to conditionally regulate the expression of a VEGF or FlGF inactivating agent by genomic deletion. For example, sflt-1 expression was suppressed by conditional Cre-lox mediated gene ablation by topical application of NLS-Cre and by corneal injection of plasmid encoding Cre recombinase (pCre) in flt-1$^{loxP/loxP}$ mouse eyes; $P<0.001$) within 2 days. Cre expression was accompanied by significantly reduced sflt-1 and increased free VEGF-A. Neither plasmid induced CV in wild-type mice. To avoid injection trauma, a cell permeable enzymatically active Cre containing a nuclear localization sequence (NLS-Cre) was delivered to the cornea by topical eye drops (FIG. 2, panels A-D). NLS-Cre, but not NLS-β-galactosidase, induced CV in flt-$1^{loxP/loxP}$ mouse eyes (P<0.001) within 2 days (FIG. 2, panels E and F). Neither NLS-enzyme induced CV in wild-type mice (FIG. 2, panels G and H).

As noted throughout the present specification, compounds that regulate the bioavailability or biological activity of VEGF or PlGF by modulating the availability of a VEGF or PLGF inactivating agent, are provided. By "modulate" or "regulate" is meant that the expression of the gene, or level of a RNA molecule or equivalent RNA molecules encoding one or more proteins or protein subunits, or activity of one or more proteins or protein subunits is up regulated or down regulated, such that expression, level, or activity is greater than or less than that observed in the absence of the modulator or regulator, i.e., a compound provided herein. For example, the term "modulate" or "regulate" can mean "inhibit," "prevent," "facilitate," or "promote," but the use of the word "modulate" or "regulate" is not limited to these definitions.

By "inhibit", "down-regulate", or "reduce", it is meant that the expression of gene encoding an inactivating agent, or level of RNA molecules or equivalent RNA molecules encoding one or more proteins or protein subunits associated with an inactivating agent, or activity of one or more proteins or protein subunits of an agent, is reduced below that observed in the absence of the compounds (e.g., siNA, antibodies, or gene ablation compounds) of the invention. In one embodiment, inhibition, down regulation, or reduction of gene expression is associated with post transcriptional silencing, such as RNAi mediated cleavage of a target nucleic acid molecule (e.g. RNA) or inhibition of translation. In one embodiment, inhibition, down regulation, or reduction of gene expression is associated with pretranscriptional silencing, such as by gene ablation.

The compounds, compositions and methods decribed herein allow for the upregulation of growth factor protein bioavialibility or biological activity by inhibiting or down-regulating the presence of a growth factor inactivating agent. By "up-regulate", or "promote", it is meant that the activity of one or more proteins or protein subunits, is increased above that observed in the absence of the nucleic acid molecules (e.g., siNA) of the invention. In one embodiment, up-regulation of growth factor bioavailability includes using a compound, such as an siNA molecule, to down regulate the availability of an inactivating reagent, such as sflt-1. The down regulation of gene expression can, for example, be induced by a coding RNA or its encoded protein, such as through negative feedback or antagonistic effects. The down regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down regulation of targets that down regulate, suppress, or inactivate a growth factor of interest can be used to up-regulate or promote the bioavailability of the growth factor of interest toward therapeutic use.

Throughout the present specification, compounds, compositions and methods are described that are useful for modulating angiogenesis an/or vasculogenesis by promoting the activity of growth factors associated with such processes. The compounds, compositions and methods generally target growth factor-inactivating agents such that the bioavailability or biological activity of a growth factor is increased.

Angiogenesis is a process of new blood vessel development from pre-existing vasculature. It plays an essential role in embryonic development, normal growth of tissues, wound healing, the female reproductive cycle (i.e., ovulation, menstruation and placental development), as well as a major role in many diseases. One of the most important growth and survival factors for endothelium is vascular endothelial growth factor (VEGF). VEGF induces angiogenesis and endothelial-cell proliferation and plays an important role in regulating vasculogenesis. VEGF is a heparin-binding glycoprotein that is secreted as a homodimer of 45 kDa. Most types of cells, but usually not endothelial cells themselves, secrete VEGF. Since the initially discovered VEGF, VEGF-A, increases vascular permeability, it was known as vascular permeability factor. In addition, VEGF causes vasodilatation, partly through stimulation of nitric oxide synthase in endothelial cells. VEGF can also stimulate cell migration and inhibit apoptosis (see "R&D Systems, Cytokine Mini Reviews, Vascular Endothelial Growth Factor (VEGF)," Copyright 2002 R&D Systems).

There are several splice variants of VEGF-A. The major ones include: 121, 165, 189 and 206 amino acids (aa), each one comprising a specific exon addition. VEGF165 is the most predominant protein, but transcripts of VEGF 121 may be more abundant. VEGF206 is rarely expressed and has been detected only in fetal liver. Recently, other splice variants of 145 and 183 aa have also been described. The 165, 189 and 206 aa splice variants have heparin-binding domains, which help anchor them in extracellular matrix and are involved in binding to heparin sulfate and presentation to VEGF receptors. Such presentation is a key factor for VEGF potency (i.e., the heparin-binding forms are more active). Several other members of the VEGF family have been cloned including VEGF-B, -C, and -D. Placenta growth factor (PlGF) is also closely related to VEGF-A. VEGF-A, -B, -C, -D, and PlGF are all distantly related to platelet-derived growth factors-A and -B. Less is known about the function and regulation of VEGF-B, -C, and -D, but they do not seem to be regulated by the major pathways that regulate VEGF-A.

VEGF-A transcription is potentiated in response to hypoxia and by activated oncogenes. The transcription factors, hypoxia inducible factor-1a (hif-1a) and -2a, are degraded by proteosomes in normoxia and stabilized in hypoxia. This pathway is dependent on the Von Hippel-Lindau gene product. Hif-1a and hif-2 a heterodimerize with the aryl hydrocarbon nuclear translocator in the nucleus and bind the VEGF promoter/enhancer. This is a key pathway expressed in most types of cells. Hypoxia inducibility, in particular, characterizes VEGF-A versus other members of the VEGF family and other angiogenic factors.

There are three receptors in the VEGF receptor family. They have the common properties of multiple IgG-like extracellular domains and tyrosine kinase activity. The enzyme domains of VEGF receptor 1 (VEGFR1, also known as Flt-1), VEGFR2 (also known as KDR or Flk-1), and VEGFR3 (also known as Flt-4) are divided by an inserted sequence. Endothelial cells also express additional VEGF receptors, Neuropilin-1 and Neuropilin-2. VEGF-A binds to VEGFR1 and VEGFR2 and to Neuropilin-1 and Neuropilin-2. PlGF and VEGF-B bind VEGFR1 and Neuropilin-1. VEGF-C and -D bind VEGFR3 and VEGFR2.

Accordingly, by "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (Biol. Reproduction, 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g., VEGF-A, VEGF-B, VEGF-C, VEGF-D, VEGF-E, VEGF189, VEGF165, or VEGF 121). Preferably, VEGF is the VEGF121 or VEGF165 isoform (Tischer et al., J. Biol. Chem. 266, 11947-11954, 1991; Neufed et al. Cancer Metastasis 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (J. Biol. Chem. 276:3222-3230, 2001). As used herein VEGF also includes any modified forms of VEGF such as those described in LeCouter et al. (Science 299:890-893, 2003). Although human VEGF is preferred, the invention is not limited to human forms and can include other animal forms of VEGF (e.g. mouse, rat, dog, or chicken). The term VEGF also refers to nucleic acid sequences encoding any vascular endothelial growth factor protein, peptide, or polypeptide having vascular endothelial growth factor activity.

By "VEGF-B" is meant, protein, peptide, or polypeptide receptor or a derivative thereof, such as encoded by Genbank Accession No. NM 003377, having vascular endothelial growth factor type B activity. The term VEGF-B also refers to nucleic acid sequences encoding any VEGF-B protein, peptide, or polypeptide having VEGF-B activity.

By "VEGF-C" is meant, protein, peptide, or polypeptide receptor or a derivative thereof, such as encoded by Genbank Accession No. NM 005429, having vascular endothelial growth factor type C activity. The term VEGF-C also refers to nucleic acid sequences encoding any VEGF-C protein, peptide, or polypeptide having VEGF-C activity.

By "VEGF-D" is meant, protein, peptide, or polypeptide receptor or a derivative thereof, such as encoded by Genbank Accession No. NM 004469, having vascular endothelial growth factor type D activity. The term VEGF-D also refers to nucleic acid sequences encoding any VEGF-D protein, peptide, or polypeptide having VEGF-D activity.

By "VEGFR" as used herein is meant, any vascular endothelial growth factor receptor protein, peptide, or polypeptide (e.g., VEGFR1, VEGFR2, or VEGFR3, including both membrane bound and/or soluble forms thereof) having vascular endothelial growth factor receptor activity. The term VEGFR also refers to nucleic acid sequences encoding any vascular endothelial growth factor receptor protein, peptide, or polypeptide having vascular endothelial growth factor receptor activity.

By "VEGFR1," "sVEGFR1," or "sflt-1" is meant, protein, peptide, or polypeptide receptor or a derivative thereof, such as encoded by Genbank Accession No. NM 002019 or GenBank accession number U01134, having vascular endothelial growth factor receptor type 1 (flt) activity, for example, having the ability to bind a vascular endothelial growth factor. The term VEGF1 also refers to nucleic acid sequences encoding any VEGFR1 protein, peptide, or polypeptide having VEGFR1 activity. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. sFlt-1 can also mean degradation products or fragments that result from enzymatic cleavage of the Flt-1 receptor and that maintain sFlt-1 biological activity. In one example, specific metalloproteinases released from the placenta may cleave the extracellular domain of Flt-1 receptor to release the N-terminal portion of Flt-1 into circulation.

A soluble form of Flt-1 (sflt-1) can be detected in peripheral blood and is a high affinity ligand for VEGF. Soluble Flt-1 can be used to antagonize VEGF function. VEGFR1 and VEGFR2 are upregulated in tumor and proliferating endothelium, partly by hypoxia and also in response to VEGF-A itself. VEGFR1 and VEGFR2 can interact with multiple downstream signaling pathways via proteins such as PLC-g, Ras, Shc, Nck, PKC and PI3-kinase. VEGFR1 is of higher affinity than VEGFR2 and mediates motility and vascular permeability. VEGFR2 is necessary for proliferation.

By "VEGFR2" is meant, protein, peptide, or polypeptide receptor or a derivative thereof, such as encoded by Genbank Accession No. NM 002253, having vascular endothelial growth factor receptor type 2 (kdr) activity, for example, having the ability to bind a vascular endothelial growth factor. The term VEGF2 also refers to nucleic acid sequences encoding any VEGFR2 protein, peptide, or polypeptide having VEGFR2 activity.

By "VEGFR3" is meant, protein, peptide, or polypeptide receptor or a derivative thereof, such as encoded by Genbank Accession No. NM 002020 having vascular endothelial growth factor receptor type 3 (kdr) activity, for example, having the ability to bind a vascular endothelial growth factor. The term VEGFR3 also refers to nucleic acid sequences encoding any VEGFR3 protein, peptide, or polypeptide having VEGFR3 activity.

In one embodiment, double stranded nucleic acid molecule of the invention is a microRNA (miRNA). By "microRNA" or "miRNA" is meant, a small double stranded RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). In one embodiment, the microRNA of the invention, has partial complementarity (i.e., less than 100% complementarity) between the sense strand or sense region and the antisense strand or antisense region of the miRNA molecule or between the antisense strand or antisense region of the miRNA and a corresponding target nucleic acid molecule. For example, partial complementarity can include various mismatches or non-base paired nucleotides (e.g., 1, 2, 3, 4, 5 or more mismatches or non-based paired nucleotides, such as nucleotide bulges) within the double stranded nucleic acid molecule, structure which can result in bulges, loops, or overhangs that result between the sense strand or sense region and the antisense strand or antisense region of the miRNA or between the antisense strand or antisense region of the miRNA and a corresponding target nucleic acid molecule.

In another embodiment, the compounds, compositions, and methods provided herein have therapeutic applications. For example, a compound, or composition that includes the compound, can be administered to a subject in order to regulate the bioavailability or biological activity of VEGF or PlGF. Accordingly, a compound provided herein is believed to find therapeutic use for treating mammals via stimulation or inhibition of growth and/or differentiation and/or activation of cells susceptible to stimulation by VEGF and/or PlGF. Exogenous compound may be administered to a patient in these circumstances. A compound of the invention is clearly useful insofar as it can be administered to a subject having depressed levels (e.g., through sequestration with an inactivating agent) of biologically active endogenous VEGF or PlGF. Such depressed levels are generally the result of VEGF or PlGF interactions with an inactivating agent. An agent-growth factor complex forms which negatively impacts the bioavailability or biological activity of VEGF and/or PlGF. Compounds provided herein reverse the effect of the inactivating agent by inhibiting, preventing or disrupting the formation of such a complex.

Accordingly, the compounds, compositions and methods provided herein can be used to treat conditions associated with decreased vascularity. For example, tissue that requires vascularization, neovascularization and/or revascularization of in a subject can be treated by a compound, composition or method provided herein. Such conditions include ocular disorders, preeclampsia, cerebrovascular disorders, cardiovascular disorders, and wound healing disorders.

By "ocular disease" as used herein is meant, any disease, condition, trait, genotype or phenotype of the eye and related structures as is known in the art, such as Cystoid Macular Edema, Asteroid Hyalosis, Pathological Myopia and Posterior Staphyloma, Toxocariasis (Ocular Larva Migrans), Retinal Vein Occlusion, Posterior Vitreous Detachment, Tractional Retinal Tears, Epiretinal Membrane, Diabetic Retinopathy, Lattice Degeneration, Retinal Vein Occlusion, Retinal Artery Occlusion, Macular Degeneration (e.g., age related macular degeneration such as wet AMD or dry AMD), Toxoplasmosis, Choroidal Melanoma, Acquired Retinoschisis, Hollenhorst Plaque, Idiopathic Central Serous Chorioretinopathy, Macular Hole, Presumed Ocular Histoplasmosis Syndrome, Retinal Macroaneursym, Retinitis Pigmentosa, Retinal Detachment, Hypertensive Retinopathy, Retinal Pigment Epithelium (RPE) Detachment, Papillophlebitis, Ocular Ischemic Syndrome, Coats' Disease, Leber's Miliary Aneurysm, Conjunctival Neoplasms, Allergic Conjunctivitis, Vernal Conjunctivitis, Acute Bacterial Conjunctivitis, Allergic Conjunctivitis & Vernal Keratoconjunctivitis, Viral Conjunctivitis, Bacterial Conjunctivitis, Chlamydial & Gonococcal Conjunctivitis, Conjunctival Laceration, Episcleritis, Scleritis, Pingueculitis, Pterygium, Superior Limbic Keratoconjunctivitis (SLK of Theodore), Toxic Conjunctivitis, Conjunctivitis with Pseudomembrane, Giant Papillary Conjunctivitis, Terrien's Marginal Degeneration, Acanthamoeba Keratitis, Fungal Keratitis, Filamentary Keratitis, Bacterial Keratitis, Keratitis Sicca/Dry Eye Syndrome, Bacterial Keratitis, Herpes Simplex Keratitis, Sterile Corneal Infiltrates, Phlyctenulosis, Corneal Abrasion & Recurrent Corneal Erosion, Corneal Foreign Body, Chemical Burs, Epithelial Basement Membrane Dystrophy (EBMD), Thygeson's Superficial Punctate Keratopathy, Corneal Laceration, Salzmann's Nodular Degeneration, Fuchs' Endothelial Dystrophy, Crystalline Lens Subluxation, Ciliary-Block Glaucoma, Primary Open-Angle Glaucoma, Pigment Dispersion Syndrome and Pigmentary Glaucoma, Pseudoexfoliation Syndrome and Pseudoexfoliative Glaucoma, Anterior Uveitis, Primary Open Angle Glaucoma, Uveitic Glaucoma & Glaucomatocyclitic Crisis, Pigment Dispersion Syndrome & Pigmentary Glaucoma, Acute Angle Closure Glaucoma, Anterior Uveitis, Hyphema, Angle Recession Glaucoma, Lens Induced Glaucoma, Pseudoexfoliation Syndrome and Pseudoexfoliative Glaucoma, Axenfeld-Rieger Syndrome, Neovascular Glaucoma, Pars Planitis, Choroidal Rupture, Duane's Retraction Syndrome, Toxic/Nutritional Optic Neuropathy, Aberrant Regeneration of Cranial Nerve III, Intracranial Mass Lesions, Carotid-Cavernous Sinus Fistula, Anterior Ischemic Optic Neuropathy, Optic Disc Edema & Papilledema, Cranial Nerve III Palsy, Cranial Nerve IV Palsy, Cranial Nerve VI Palsy, Cranial Nerve VII (Facial Nerve) Palsy, Horner's Syndrome, Internuclear Ophthalmoplegia, Optic Nerve Head Hypoplasia, Optic Pit, Tonic Pupil, Optic Nerve Head Drusen, Demyelinating Optic Neuropathy (Optic Neuritis, Retrobulbar Optic Neuritis), Amaurosis Fugax and Transient Ischemic Attack, Pseudotumor Cerebri, Pituitary Adenoma, Molluscum Contagiosum, Canaliculitis, Verruca and Papilloma, Pediculosis and Pthiriasis, Blepharitis, Hordeolum, Preseptal Cellulitis, Chalazion, Basal Cell Carcinoma, Herpes Zoster Ophthalmicus, Pediculosis & Phthiriasis, Blow-out Fracture, Chronic Epiphora, Dacryocystitis, Herpes Simplex Blepharitis, Orbital Cellulitis, Senile Entropion, and Squamous Cell Carcinoma.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20th week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (by dipstik on urinanaysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100000 cells/ul), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

Several factors have been-reported to have an association with fetal and placental development and, more specifically, with pre-eclampsia. They include vascular endothelial growth factor (VEGF), soluble Flt-1 receptor (sFlt-1), and placental growth factor (PlGF). As previously noted, VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

By "cardiovascular disorders" is meant cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cortriatriatum, coronary vessel anomalies, crisscross heart, dextrocardia, patent, ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include, but are not limited to, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial fluner, bradycardia, extrastole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Myocardial diseases include, but are not limited to, alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include, but are not limited to, dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include, but are not limited to, arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include, but are not limited to, air embolisms, amniotic fluid embolisms, cholesterol embolisms, blue toe syndrome, fat embolisms, pulmonary embolisms, and thromboembolisms. Thrombosis include, but are not limited to, coronary thrombosis, hepatic vein thrombosis, retinal vein occlusion, carotid artery thrombosis, sinus thrombosis, Wallenberg's syndrome, and thrombophlebitis.

Ischemic disorders include, but are not limited to, cerebral ischemia, ischemic colitis, compartment syndromes, anterior compartment syndrome, myocardial ischemia, reperfusion injuries, and peripheral limb ischemia. Vasculitis includes, but is not limited to, aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

By "wound healing" is meant any disorder, disease or injury associated with a tissue that would benefit from increased vascularization. Accordingly, "wound healing" encompasses facilitating angiogenesis in the context vascularization of, for example, grafts, organ transplantation, or any other activity associated with tissue regeneration. Various potential therapeutic uses of a compound include those in which increasing the bioavailability of VEGF or PlGF is useful. Examples of these include uses associated with the vascular endothelium, such as the treatment of traumata to the vascular network, in view of the demonstrated rapid promotion by VEGF of the proliferation of vascular endothelial cells that would surround the traumata. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, hemophiliac, and varicose ulcers. Other physiological conditions that could be improved based on the selective mitogenic character of the compound are also included herein.

For the traumatic indications referred to above, the compound will be formulated and dosed in a fashion consistent with good medical practice taking into account the specific disorder to be treated, the condition of the individual patient, the site of delivery of the compound, the method of administration, and other factors known to practitioners. Accordingly, the compound can be included in a composition, such as a pharmaceutically-acceptable composition, for administration to the site of trauma.

Additional indications for compounds provided herein include the treatment of full-thickness wounds such as dermal ulcers, including the categories of pressure sores, venous ulcers, and diabetic ulcers, as well as of full-thickness burns and injuries where angiogenesis is required to prepare the burn or injured site for a skin graft or flap. In this case the compound is either applied directly to the site or it is used to soak the skin or flap that is being transplanted prior to grafting. In a similar fashion, the compound can be used in plastic surgery when reconstruction is required following a burn or other trauma, or for cosmetic purposes.

Angiogenesis is also important in keeping wounds clean and non-infected. The compound can therefore be used in association with general surgery and following the repair of cuts and lacerations. It is particularly useful in the treatment of abdominal wounds with a high risk of infection. Neovascularization is also key to fracture repair, since blood vessels develop at the site of bone injury. Administration of the compound to the site of a fracture is therefore another utility.

In cases where the compound is being used for topical wound healing, as described above, it may be administered by any of the routes described below for the re-endothelialization of vascular tissue, or more preferably by topical means. In these cases, it will be administered as either a solution, spray, gel, cream, ointment, or dry powder directly to the site of injury. Slow-release devices directing the compound to the injured site will also be used. In topical applications, the compound will be applied at a concentration ranging from about 50 to 1,000 ug/mL, either in a single application, or in dosing regimens that are daily or every few days for a period of one week to several weeks. Generally, the amount of topical formulation administered is that which is sufficient to apply from about 0.1 to 100 ug/cm$^2$ of the compound, based on the surface area of the wound.

The compound can be used as a post-operative wound healing agent in balloon angioplasty, a procedure in which vascular endothelial cells are removed or damaged, together with compression of atherosclerotic plaques. The compound can be applied to inner vascular surfaces by systemic or local intravenous application either as intravenous bolus injection or infusions. If desired, the compound can be administered over time using a micrometering pump. Suitable compositions for intravenous administration comprise the compound in an amount effective to promote endothelial cell growth and a parenteral carrier material. The compound can be present in the composition over a wide range of concentrations, for example, from about 50 ug/mL to about 1,000 ug/mL using injections of 3 to 10 mL per patient, administered once or in dosing regimens that allow for multiple applications. Any of the known parenteral carrier vehicles can be used, such as normal saline or 5-10% dextrose.

The compound can also be used to promote endothelialization in vascular graft surgery. In the case of vascular grafts using either transplanted vessels or synthetic material, for example, the compound can be applied to the surfaces of the graft and/or at the junctions of the graft and the existing vasculature to promote the growth of vascular endothelial cells. For such applications, the compound can be applied intravenously as described above for balloon angioplasty or it can be applied directly to the surfaces of the graft and/or the existing vasculature either before or during surgery.

By "Pharmaceutically acceptable composition" or "therapeutic formulation" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20th edition), ed. A. Gennaro, 2000, Lippincott, Williams & Wilkins, Philadelphia, Pa.

Such compositions are prepared for storage by mixing compound having the desired degree of purity with optional physiologically acceptable carriers, excipients, or stabilizers (Remington's Pharmaceutical Sciences, 16th edition, Osol, A., Ed., [1980]), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The compound also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles, and nanocapsules), or in macroemulsions.

In general, a compound to be used for in vivo administration must be sterile. This is readily accomplished by filtration through sterile filtration membranes, prior to or following lyophilization and reconstitution. compound ordinarily will be stored in lyophilized form or in solution.

Therapeutic compound compositions generally are placed into a container having a sterile access port, for example, an intravenous solution bag or vial having a stopper pierceable by a hypodermic injection needle.

The route of compound administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. A compound provided herein can be administered continuously by infusion or by bolus injection. Generally, where the disorder permits, one should formulate and dose the compound for site-specific delivery. This is convenient in the case of wounds and ulcers. Suitable examples of sustained-release preparations include semi-permeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethyl-methacrylate) as described by Langer et al., J. Biomed. Mater. Res., 15:167, 1981 and Langer, Chem. Tech., 12:98, 1982 or poly(vinylalcohol)], polylactides (U.S. Pat. No. 3,773,919, EP 58,481), copolymers of L-glutamic acid and gamma ethyl-L-glutamate (Sidman et al., Biopolymers, 22:547, 1983), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated compounds remain in the body for an extended period of time, they may denature or aggregate as a result of exposure to moisture at 37° C., resulting in a loss of biological activity. Rational strategies can be devised for nucleic acid and/or protein stabilization depending on the mechanism involved.

Sustained-release compound compositions also include liposomally entrapped compound. Liposomes containing compound are prepared by methods known per se: DE 3,218,121; Epstein et al., Proc. Natl. Acad. Sci. USA, 82:3688-3692 (1985); Hwang et al., Proc. Natl. Acad. Sci. USA, 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol % cholesterol, the selected proportion being adjusted for the optimal compound therapy.

When applied topically, the compound is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the compound formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalky celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the compound held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the compound is present in an amount of about 300-1000 mg per ml of gel.

An effective amount of compound to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the compound until a dosage is reached that achieves the desired effect. A typical daily dosage for systemic treatment might range from about 1 ug/kg to up to 10 mg/kg or more, depending on the factors mentioned above. As an alternative general proposition, the compound is formulated and delivered to the target site or tissue at a dosage capable of establishing in the tissue a compound level greater than about 0.1 ng/cc up to a maximum dose that is efficacious but not unduly toxic. This intra-tissue concentration should be maintained if possible by continuous infusion, sustained release, topical application, or injection at empirically determined frequencies. The progress of this therapy is easily monitored by conventional assays.

It is within the scope hereof to combine "compound therapy" with other novel or conventional therapies (e.g., growth factors such as VEGF, PlGF, acidic or basic fibroblast growth factor (aFGF or bFGF, respectively), platelet-derived growth factor (PDGF), insulin-like growth factor (IGF-I or IGF-II), nerve growth factor (NGF), anabolic steroids, EGF or TGF-alpha) for enhancing the activity of any of the growth factors, including the compound, in promoting cell proliferation and repair.

It is not necessary that such co-treatment drugs be included per se in the compositions of this invention, although this will be convenient where such drugs are proteinaceous. Such admixtures are suitably administered in the same manner and for the same purposes as the compound used alone. The useful molar ratio of compound to such secondary growth factors is typically 1:0.1-10, with about equimolar amounts being preferred.

As discussed throughout the present specification, the inventors have identified a unique interaction between growth factors and inactivating agents in ocular tissue. The interaction effectively results in the inactivation of the growth factors by sequestration in complexes. In view of this discovery, the present specification not only provides novel compounds for regulating the bioavailability of growth factors, but also provides mechanisms for identifying additional compounds which modulate such interactions. Accordingly, based on these discoveries, any number of methods are available for carrying out screening assays to identify new candidate compounds that alter the ability of an inactivating agent to sequester a growth factor.

Thus, in another embodiment, provided herein are methods of identifying a compound that regulates the bioavailability or biological activity of VEGF or PlGF in vivo or in situ. In general, the method includes contacting corneal tissue with a test compound that regulates, or is believed to regulate, the expression of a VEGF or PlGF inactivating agent, or the ability of the VEGF or PlGF inactivating agent to bind to VEGF or PlGF. The bioavailability or biological activity of VEGF or PlGF can be measured and the compound identified by its effect on the bioavailability or biological activity of VEGF or PlGF.

There is provided a method for screening candidate compounds that modulate the ability of an inactivating agent to interact with VEGF or PlGF thereby promoting vascularization in a tissue, such as ocular or placental tissue. Preferably, the test compound prevents, inhibits or disrupts the ability of an FLT gene product to interact with VEGF or PlGF and inhibit or antagonize VEGF or PlGF activity. In this aspect of the invention, ocular tissue associated with, or derived from, a test animal, such as a mouse, rat, rabbit, monkey, pig, etc. can be used in the screening method. The candidate drug or test compound is administered to the ocular tissue at various times and at various locations (as described throughout the specification). Subsequently, the tissue is monitored for the appearance of neovascularization, or for an increase on the bioavailability or biological activity of a growth factor such as VEGF.

Exemplary test compounds include siNA molecules that are active in mediating RNA interference against a VEGF and/or PlGF inactivating agent. Additional exemplary test compounds include organic molecules, peptides, peptide mimetics, polypeptides, nucleic acids, and antibodies that bind to a soluble inactivating agent. Optionally, compounds identified in any of the assays described herein may be confirmed as useful in an assay for compounds that increase the bioavailability or biological activity of VEGF or PlGF.

In general, compounds capable of decreasing the inactivating activity of an agent can be identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

EXAMPLES

The invention is illustrated in the following examples, which are provided by way of illustration and are not intended to be limiting.

Corneal avascularity is required for optical clarity and optimal vision and has enabled the cornea to become the lead platform for validating pro- and anti-angiogenic strategies for myriad disorders. Yet the molecular underpinnings of the avascular phenotype have until now remained obscure and are all the more remarkable given the presence of vascular endothelial growth factor (VEGF)-A, a potent stimulator of angiogenesis, in the cornea and its proximity to vascularized tissues. The present studies show that the cornea expresses soluble VEGF receptor-1 (sVEGFR-1; 1 also known as sflt-1) and that suppression of this endogenous VEGF-A trap by neutralizing antibodies, RNA interference, or Cre-lox mediated gene disruption abolishes corneal avascularity in mice.

The spontaneously vascularized corneas of corn1 and Pax6$^{+/-}$ mice and Pax6$^{+/-}$ patients with aniridia are deficient in sflt-1. Recombinant sflt-1 administration rescues corneal avascularity in corn1 and Pax6$^{+/-}$ mice. Manatees, the only known creatures to uniformly have vascularized corneas, do not express sflt-1, whereas the avascular corneas of dugongs, also members of the order Sirenia, elephants, the closest extant terrestrial phylogenetic relatives of manatees, and other marine mammals (dolphins, whales) contain sflt-1, indicating a crucial, evolutionarily conserved role. The recognition that sflt-1 is essential to shielding vascular apartheid in the cornea provides a platform for modulating angiogenesis and treating neovascular diseases.

Despite its widespread use as a readout template, the molecular foundations of corneal avascularity remain nebulous. In the last decade numerous anti-angiogenic molecules such as angiostatin, endostatin, interleukin-1 receptor antagonist, pigment epithelium derived factor, and thrombospondins were identified in the cornea (reviewed in Chang et al., Curr. Opin. Ophthalmol. 12:242, 2001), leading to recognition of their tumor suppressive, atherosclerotic plaque growth inhibitory, or wound healing modulatory roles. None of these molecules, however, are singly requisite for corneal avascularity because mice deficient in any of them retain normal corneal phenotypes, engendering the view of multiply redundant mechanisms of corneal avascularity. The search for angiogenesis inhibitors to treat atherosclerosis, cancer, diabetic kidney and retina damage, macular degeneration, and rheumatoid arthritis often relies on initial efficacy testing in the cornea for it is exquisitely devoid of blood vessels despite being surrounded by the highly vascular conjunctiva (FIG. 1, panel A). The cornea is ideal for understanding the ability of tissues to demarcate vascular ingrowth and identifying efficacy of therapies against known angiogenic stimuli.

The present studies have determined, for the first time, that the cornea contained VEGF-A, but nearly all of it was bound (FIG. 1, panel B). To reconcile the paradoxical presence of this potent pro-angiogenic molecule in an avascular tissue, a counterbalancing expression of sflt-1 was identified. sflt-1 is an alternatively spliced secreted isoform of membrane bound flt-1 (mbflt-1), a cell surface receptor. sflt-1 lacks the transmembrane (tm) and tyrosine kinase (tk) domains and can act as a manacle for VEGF-A (Kendall & Thomas, Proc. Natl. Acad. Sci. USA, 90:10705, 1993). sflt-1 mRNA and protein were identified in the cornea (FIG. 1, panels C-G); in contrast, mbflt-1 was present in the conjunctiva but not detectable in the cornea (FIG. 1, panel G). sflt-1 was present extracellularly. In vivo interaction between sflt-1 and VEGF-A was confirmed by immunoprecipitation (FIG. 1, panel H) and corroborated by immunostaining.

sflt-1 preservation of corneal avascularity was confirmed in mice. First, corneal injections of neutralizing antibody against flt-1 were performed with fellow eyes receiving isotype control antibody. Eyes treated with blocking antibody consistently developed corneal vascularization (CV) from the limbus within 1 day, whereas those treated with control antibody did not (P<0.001). Free VEGF-A was greater in anti-flt-1 antibody-treated corneas than in control treated corneas, indicating that sequestration of VEGF-A by sflt-1 maintains corneal avascularity. This was confirmed by demonstrating that concomitantly treating corneas with neutralizing anti-VEGF-A antibody, but not with isotype-control antibody, prevented CV induced by the anti-flt-1 antibody (P=0.029). Because the anti-flt-1 antibody would theoretically block ligand-binding of both mbflt-1 and sflt-1 (although the former is undetectable in the cornea), this antibody was tested in flt-1 tyrosine kinase$^{-/-}$ (flt-1 tk$^{-/-}$) mice, which are deficient in receptor ligation induced signaling. The anti-flt-1 antibody, but not control, induced CV in flt-1 tk$^{-/-}$ eyes as well (P=0.029), indicating that the vascular phenotype resulted from suppression of sflt-1 function and not interference with flt-1 signaling. Subconjunctival injection of anti-flt-1 antibody, which eliminates the confounding effect of corneal trauma, also elicited CV (P=0.008).

Figure 2:
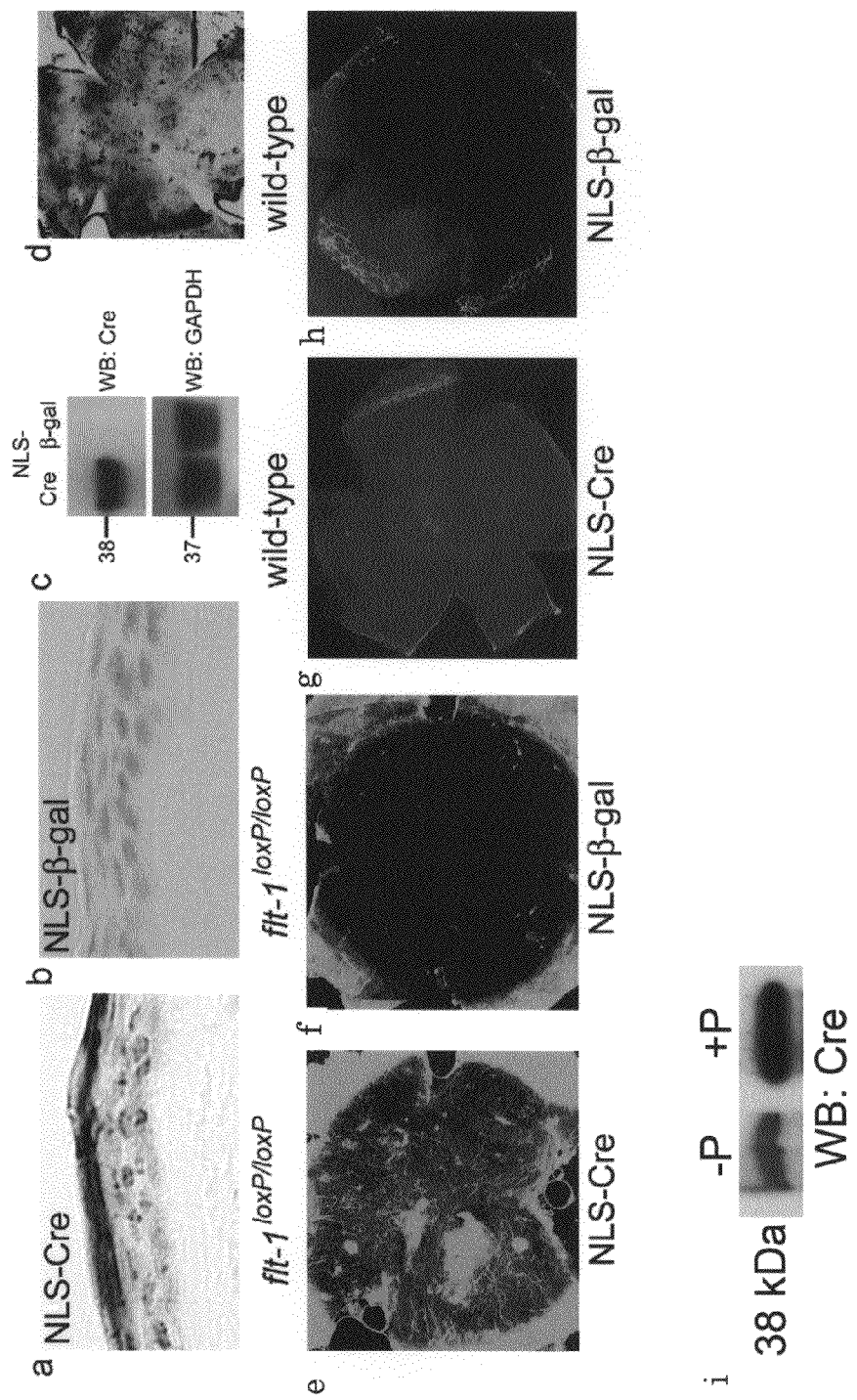
FIG. 2, panel A depicts topical enzymatically active Cre recombinase abolishes corneal avascularity in flt-1$^{loxP/loxP}$ mice. NLS-Cre induces Cre expression (brown) in the cornea within 1 hour of eye drop application as demonstrated by immunolocalization in cell nuclei.

In another embodiment, sflt-1 expression was conditionally regulated by genomic deletion. sflt-1 expression was suppressed by conditional Cre-lox mediated gene ablation because flt-1 deletion is lethal. Corneal injection of plasmid encoding Cre recombinase (pCre), but not of pNull, induced CV in flt-1$^{loxP/loxP}$ mouse eyes (P<0.001) within 2 days. Cre expression was accompanied by significantly reduced sflt-1 and increased free VEGF-A. Neither plasmid induced CV in wild-type mice. To avoid injection trauma, a cell permeable enzymatically active Cre containing a nuclear localization sequence (NLS-Cre) was delivered to the cornea by topical eye drops (FIG. 2, panels A-D). NLS-Cre, but not NLS-β-galactosidase, induced CV in flt-1$^{loxP/loxP}$ mouse eyes (P<0.001) within 2 days (FIG. 2, panels E and F). Neither NLS-enzyme induced CV in wild-type mice (FIG. 2, panels G and H).

In another embodiment, sflt-1 expression was regulated using RNA interference (RNAi) via corneal injection of plasmid expressing a short hairpin RNA (shRNA) targeted against a sequence in the unique carboxyl-terminus region of sflt-1 (pshRNA-sflt-1). The control was plasmid expressing a shRNA targeted against a sequence in the unique carboxyl-terminus region of mbflt-1 not present in sflt-1 (pshRNA-mbflt-1). pshRNA-sflt-1, but not pshRNA-mbflt-1, substantially reduced both sflt-1 mRNA and protein, indicating that knockdown was through RNAi (FIG. 3, panels A and B), and increased free VEGF-A (FIG. 3, panel C), corroborating the thesis that sflt-1 sequesters VEGF-A to maintain physiological avascularity. pshRNA-sflt-1, but not pshRNA-mbflt-1, consistently induced CV within 3 days after injection (P<0.0001) (FIG. 3, panels D-F). pshRNA-sflt-1 also induced CV in mice systemically depleted of macrophages and neutrophils by clodronate liposomes and anti-Gr-1 antibody, indicating that CV was not induced by infiltration of inflammatory cells and their delivery of VEGF-A. Further, pshRNA-sflt-1 did not elevate VEGF-A mRNA.

In addition to sflt-1, the transmembrane domain of flt-1 (flt-1-TM) also can trap VEGF-A. flt-1 tk$^{-/-}$ mice (n>60), which retain expression of sflt-1 and flt-1-TM, have avascular corneas just as wild-type mice. pshRNA-sflt-1, but not pshRNA-mbflt-1, induced CV in flt-1 tk$^{-/-}$ eyes (P=0.029) just as in wild-type eyes, indicating that sflt-1 and not flt-1-TM is required for corneal avascularity.

Apart from VEGF-A, sflt-1 also binds VEGF-B and placenta growth factor (PlGF). Expression of these alternate ligands in mouse corneas was much less than that of VEGF-A. Moreover, pshRNA-sflt-1, but not pshRNA-mbflt-1, induced CV both in Vegfb$^{-/-}$ (P=0.029) and Plgf$^{-/-}$ (P<0.0001) mice, supporting the contention that CV results from desequestration of VEGF-A from sflt-1. Direct evidence for this assertion was obtained by demonstrating that CV induced by pshRNA-sflt-1 in wild-type mice was prevented by a neutralizing anti-VEGF-A antibody but not by isotype-control antibody (P=0.008).

pshRNAs can inhibit gene expression nonspecifically via interferon (IFN)-mediated responses; however, pshRNA-sflt-1 induced CV in Ifnar1$^{-/-}$ and Ifng$^{-/-}$ mice just as in wild-type mice, indicating that CV was not attributable to IFN response effectors. To examine whether other off-target effects might be responsible for CV induced by pshRNA-sflt-1, a p$_2$shRNA-sflt-1 targeted against a different sequence in the unique carboxyl terminus region of sflt-1 was synthesized. Corneal injection of p$_2$shRNA-sflt-1 also induced CV in wild-type mice, making it unlikely that off-target effects, which are sequence-specific and not target-specific, were responsible for loss of corneal avascularity.

To confirm that CV induced by pshRNA-sflt-1 was mechanistically linked to sflt-1 knockdown, a plasmid coding for a "hardened-target" version of sflt-1 (psflt-1*) containing seven translationally silent wobble position mutations rendering expressed sflt-1 refractory to pshRNA-sflt-1 was developed. psflt-1*, but not psflt-1, prevented suppression of sflt-1 and CV development in eyes treated with pshRNA-sflt-1 (P=0.008); this functional control definitively established that the angiogenic phenotype was due to RNAi-mediated knockdown of sflt-1. Genetic, transcriptional, and protein-targeting suppression of sflt-1 all induced CV, demonstrating that sflt-1 is the preeminent molecular defender of corneal avascularity.

The cornea remains avascular even in states of hypoxia such as those induced by eyelid closure during sleep or coma, and a variety of ischemic and occlusive disease states. We examined VEGF-A and sflt-1 levels in corneas of mice exposed to 8% $O_2$ (comparable to corneal hypoxia during sleep) for 24 hours. Despite profound hypoxia, these corneas remained avascular. Although hypoxia can increase VEGF-A production, free VEGF-A was not significantly elevated in hypoxic corneas (11±23% greater than non-hypoxic corneas; P=0.78). This was attributed to a 86±34% increase in sflt-1 in hypoxic corneas (P=0.05), consistent with the presence of a hypoxia-responsive element in the flt-1 gene. These data confirm an important protective role upon sflt-1 in maintaining corneal avascularity during physiological hypoxia. In contrast, VEGF-A elevation without concomitant sflt-1 induction, modeled by injection of recombinant VEGF-A, was reversed by recombinant sflt-1/Fc administration but not isotype control IgG/Fc, confirming its specificity.

Figure 4:
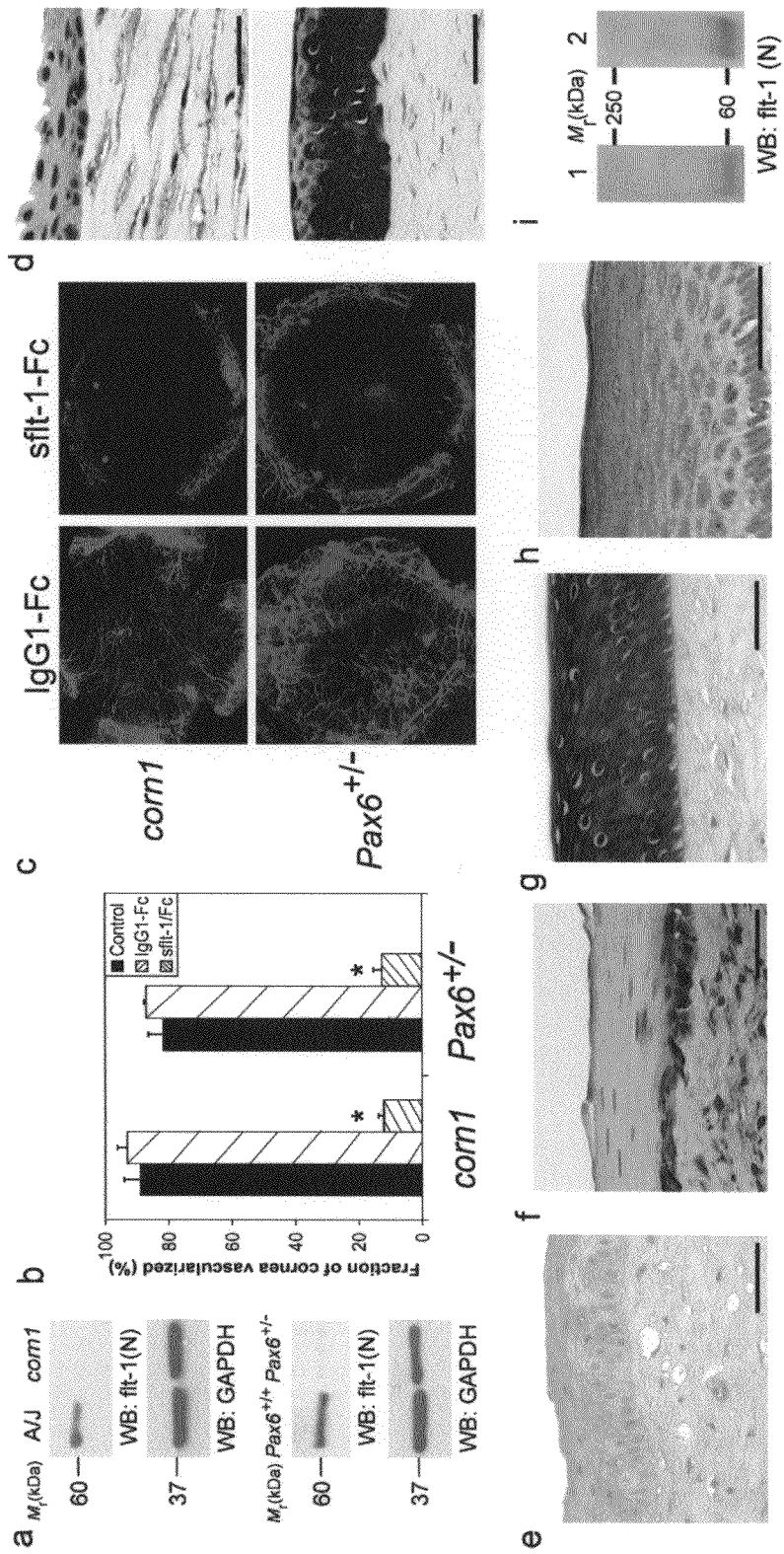
FIG. 4, panel A provides reducing western blots showing a deficiency of sflt-1 in corneas of corn1 and Pax6$^{+/-}$ mice compared to background strain A/J and Pax6$^{+/+}$ mice.
Figure 5:
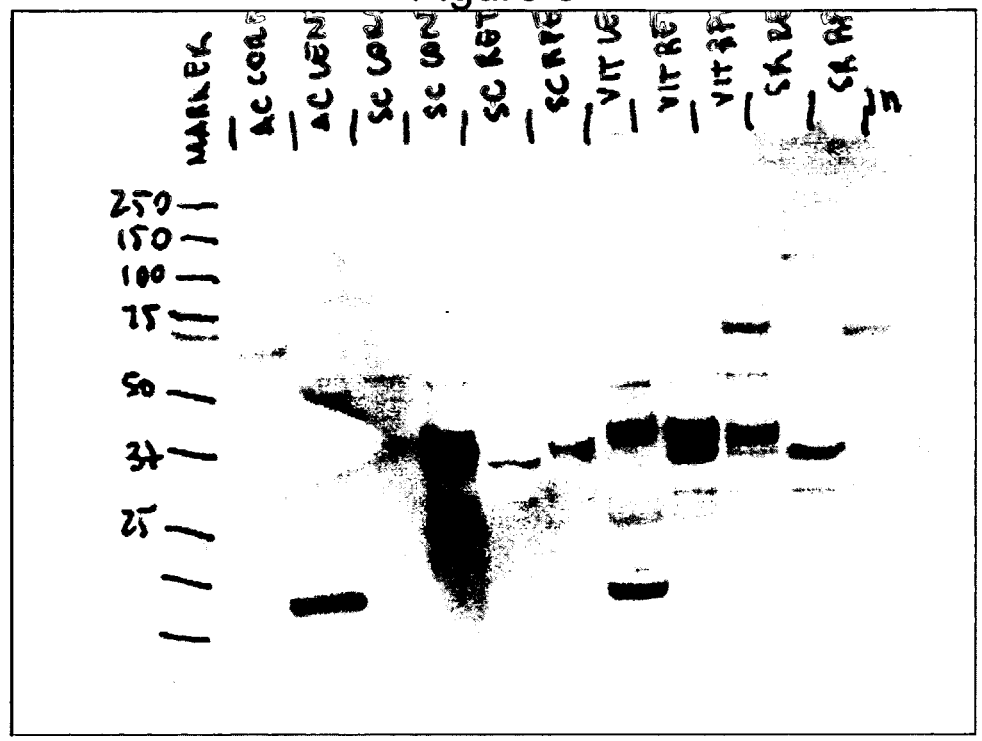
FIG. 5 depicts a reducing western blot of Cre expression showing that 1) AC injection of NLS-Cre leads to corneal expression of Cre; 2) SC injection leads to expression in the cornea, retina, and RPE/choroid; 3) VIT injection leads to expression in lens, retina, and RPE/choroid; and 4) SR injection leads to expression in retina and RPE/choroid over 1 hr.
Figure 6:
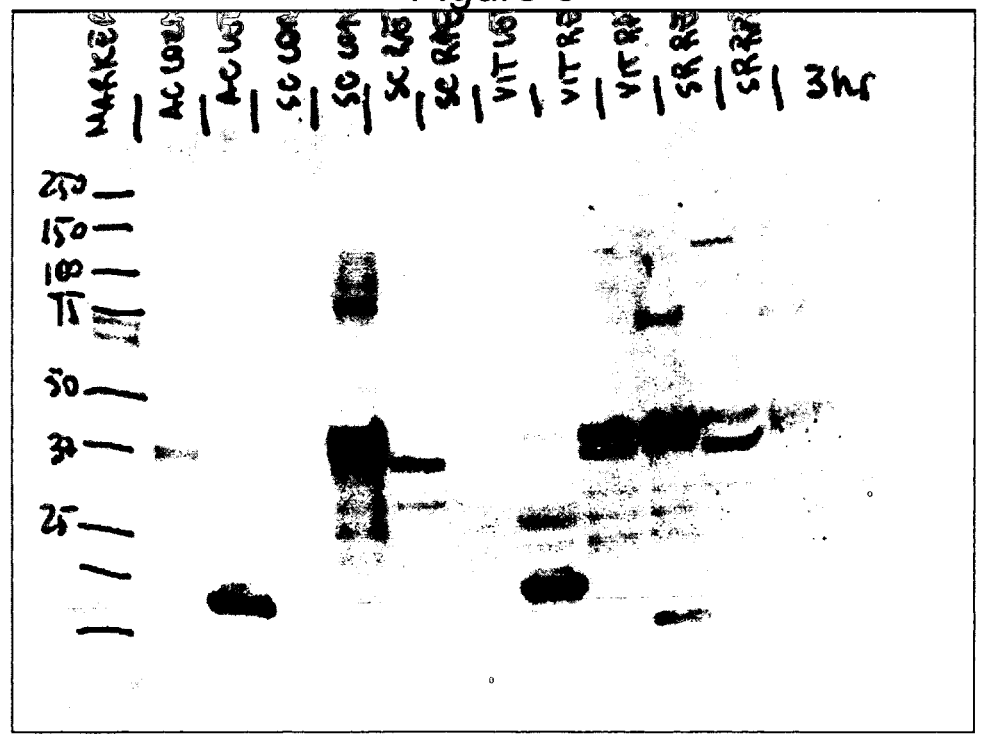
FIG. 6 depicts a reducing western blot of Cre expression showing that 1) AC injection of NLS-Cre leads to corneal expression of Cre; 2) SC injection leads to expression in the cornea, retina, and RPE/choroid; 3) VIT injection leads to expression in lens, retina, and RPE/choroid; and 4) SR injection leads to expression in retina and RPE/choroid over 3 hrs.
Figure 7:
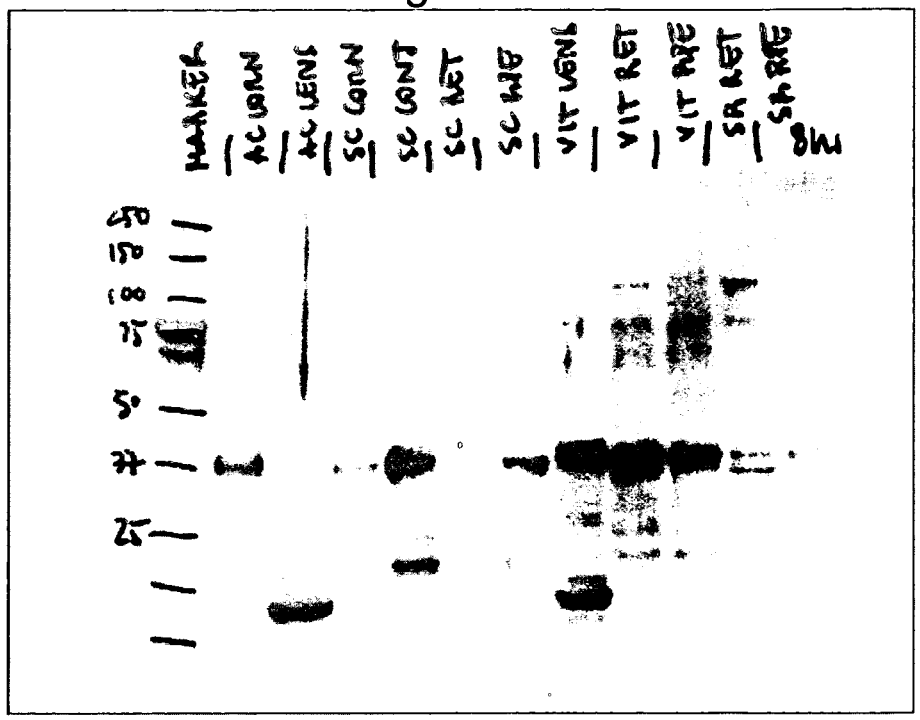
FIG. 7 depicts a reducing western blot of Cre expression showing that 1) AC injection of NLS-Cre leads to corneal expression of Cre; 2) SC injection leads to expression in the cornea, retina, and RPE/choroid; 3) VIT injection leads to expression in lens, retina, and RPE/choroid; and 4) SR injection leads to expression in retina and RPE/choroid over 8 hrs.
Figure 8:
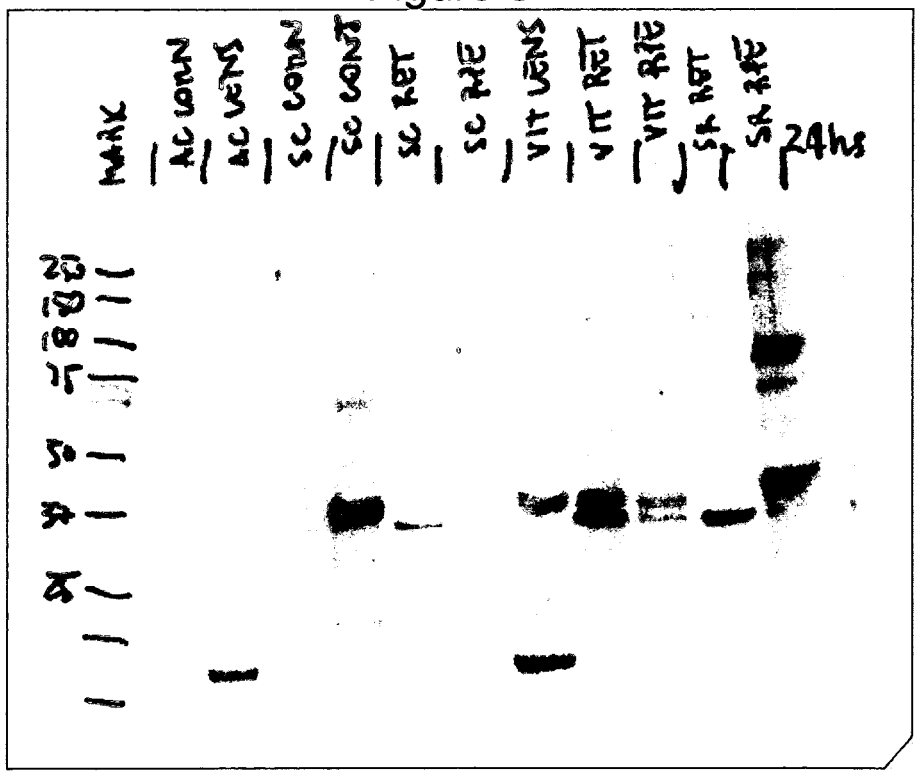
FIG. 8 depicts a reducing western blot of Cre expression showing that 1) AC injection of NLS-Cre leads to corneal expression of Cre; 2) SC injection leads to expression in the cornea, retina, and RPE/choroid; 3) VIT injection leads to expression in lens, retina, and RPE/choroid; and 4) SR injection leads to expression in retina and RPE/choroid over 24 hrs.

The spontaneously vascularized corneas of corn1 and Pax6$^{+/-}$ mice were examined for the presence of sflt-1. Corneas of corn1 and Pax6$^{+/-}$ mice, unlike those of their background strains, were deficient in sflt-1 (FIG. 4, panel A). It is notable that both strains have abnormalities in their corneal epithelium, the predominant source of sflt-1. sflt-1/Fc injection significantly reduced CV area in corn1 and Pax6$^{+/-}$ mice compared to both IgG/Fc treated and untreated corneas, both conferring a significant role for sflt-1 in maintaining corneal homeostasis and suggesting the potential to clinically rescue CV. Although mutations in destrin, the protein altered in corn1 mice, have not been reported in humans, Pax6 mutations are present in patients with aniridia, who also have CV. Interestingly aniridic patient corneas were deficient in sflt-1 compared to normal human corneas (FIG. 4, panel D).

Florida manatees (*Trichechus manatus latirostris*) are the only organisms reported to uniformly have spontaneously vascularized corneas. This phenotype was also observed in the Antillean manatee (*Trichechus manatus manatus*). Interestingly neither manatee cornea expressed sflt-1 whereas the avascular corneas of dugongs (*Dugong dugon*), which also belong to order Sirenia, and of Asian (*Elephas maximus*) and African (*Loxodanta africana*) elephants, the closest extant terrestrial phylogenetic relatives of manatees, did (FIG. 4, panels E-G). The avascular corneas of other marine mammals such as dolphins (bottlenose: *Tursiops truncatus*; Risso's: *Grampus griseus*), and whales (Cuvier's beaked: *Ziphius cavirostris*; fin: *Balaenoptera physalus*; melon-headed: *Peponocephala electra*) also contained sflt-1 (FIG. 4, panels H and I). The correlation between sflt-1 expression and corneal avascularity in diverse mammals supports an evolutionarily conserved role for sflt-1 conferring the cloak of corneal avascularity. Unlike dolphin and elephant corneas (FIG. 4, panel I), manatee corneas expressed mbflt-1, suggesting a splicing switch potentially accounting for their vascularized state. The teleological basis of the vascularized manatee cornea is intriguing. The absence of corneal sflt-1 and potentially sub-optimal vision might result from a non-deleterious mutation in manatees as they live primarily in turbid waters. Unlike dugongs which are strictly marine, manatees are believed to be physiologically dependent on freshwater and CV could protect against, or perhaps result from, irritations of this hypotonic environment.

The presence of numerous anti-angiogenic molecules in the cornea suggests multiply redundant mechanisms for maintaining avascularity, which is essential for optical transparency and clear vision. Therefore the finding that neutralization or knockdown of sflt-1 alone abolishes corneal avascularity is surprising but consistent with the presence of VEGF-A in the normal cornea. VEGF-A may be produced and held in a sequestered state by the cornea as a readily available store because this exposed tissue is susceptible to injuries potentially requiring an angiogenic response. Alternatively it might be a vestigial residue of an evolutionary requirement to provide blood to the eye that later required biochemical compensation in the form of sflt-1 expression to support improved vision.

The utilization of sflt-1 to regulate VEGF-A bioavailability is conserved in other systems such as cyclic vascularization and embryonic sprouting, and disturbances in this regulation underlie preeclampsia. The present data identify a new role for sflt-1 in evolutionary establishment of optimal vision resulting from and requiring optical clarity. Apart from trapping VEGF-A, sflt-1 can heterodimerize with mbflt-1 and VEGFR-2. Although neither mbflt-1 nor VEGFR-2 is expressed in the normal cornea (FIG. 1, panel G), such heterodimerization can modulate pathological CV. Other mechanisms of regulating VEGF-A bioavailability, such as matrix metalloproteinase-induced release, have been identified in a tumor angiogenesis model (Bergers et al., Nat. Cell. Biol. 2:737, 2000).

The cornea has long been used as a readout platform to assay anti-angiogenic therapy in oncology, cardiovascular biology, and other fields. The recognition that sflt-1 is dominant in maintaining corneal avascularity directly impacts the generalizability of this tissue in individual models. The present data elucidates the immunologic privilege of the cornea as corneal avascularity is critical to the high success of corneal allografts. The present findings also support the use of sflt-1 in preventing or treating neovascularization. Furthermore, they illuminate its potential as a therapeutic target in conditions where inducing angiogenesis in a sflt-1-rich microenvironment might be beneficial, e.g., preeclampsia, wound healing, stroke, and heart disease.

In vivo images were captured by CCD camera (Nikon) under a dissecting microscope. Blood vessels were defined by positive labeling with FITC-conjugated rat antibody against mouse CD31 (1:333; BD Pharmingen) and negative labeling with rabbit antibody against mouse LYVE-1 (1:333; Abcam) on corneal flat mounts as previously reported.

Neutralizing goat antibody (10 μg) against mouse flt-1 (R&D Systems), isotype control goat IgG (10 μg; Jackson Immunoresearch), shRNAs (4 μg) against mbflt-1 or sflt-1, psflt-1 (4 μg), psflt-1* (4 μg), pCre (4 μg), pNull (4 μg), rmVEGF-$A_{164}$ (20-500 ng; R&D Systems), sflt-1/Fc (5 μg; R&D Systems), or isotype control IgG1/Fc (5 μg; Jackson Immunoresearch) were injected (2 μl) into the cornea with a 33 gauge needle. Corneal transfection efficiency by naked plasmid of pGFP or placZ exceeded 70% as gauged by flow cytometry and Xgal staining. Tail vein injection of clodronate liposomes (200 μl) and intraperitoneal injection of anti-Gr-1 antibody (200 μg; eBioscience) were performed on each of the two days before and immediately after corneal injection of pshRNA sflt-1 injection to deplete peripheral monocytes/macrophages and neutrophils.

A/J, C57Bl/6J, corn1, Ifng$^{-/-}$, ROSA26R (Gt(ROSA)$_{26}$ Sor$^{tm1Sor}$/J) lacZ reporter (The Jackson Laboratory), Vegfb$^{-/-}$ (The Jackson Laboratory), and Balb/c mice (Harlan Laboratories) were used. Ifnar1$^{-/-}$, Pax6$^{+/-}$, Pax6$^{+/+}$, and Plgf$^{-/-}$ mice have been previously described (Muller, U. et al., Science 264:1918, 1994; Quinn et al., Genes Dev 10:435, 1996; Carmeliet et al., Nat. Med. 7:575, 2001). flt-1$^{loxP/loxP}$ mice, generated and characterized by Genentech, are described elsewhere. Dolphin, dugong, elephant, human, manatee, and whale eyes were collected in accordance with applicable regulations. Experiments were approved by institutional review boards and conformed to the Association for Research in Vision and Ophthalmology Statement on Animal Research.

Hypoxia was induced by placing C57Bl/6J mice into 8% $O_2$ PEGASS chambers (Columbus Instruments) for 24 hours.

siRNA expression cassettes (SECs) were developed by in vitro amplification by PCR. Exemplary siRNA sequences include:

| | |
|---|---|
| AAACAACCACAAAAUACAACA | (SEQ ID NO: 1) |
| AATGATTGTACCACACAAAGT | (SEQ ID NO: 2) |
| TCTCGGATCTCCAAATTTA | (SEQ ID NO: 3) |
| AAAGGCTGTTTTCTCTCGGAT | (SEQ ID NO: 4) |
| AAAAGCACAAGGAATGATTGT | (SEQ ID NO: 5) |
| AAAGGCCATTTTCTCTCGGAT | (SEQ ID NO: 6) |
| AAAAGCAGGAGGAATGATTGT | (SEQ ID NO: 7) |

It is understood that the present methods and compositions encompass the complement sequence of any of the above identified sequences. The invention also encompasses sequences where "U" (uracil) is substituted for "T" (thymine).

Multiple sequences were screened to identify the best targets for mbflt-1 (e.g., AAACAACCACAAAAUACAACA (SEQ ID NO:1)) and sflt-1 (e.g., AAUGAUUGUACCACA-CAAAGU (SEQ ID NO:13); and UCUCGGAUCUCCA-AAUUUA (SEQ ID NO:14)), which were ligated into the pSEC Neo vector. Plasmids were prepared (Plasmid Mini Prep kit, Eppendorf) and sequenced to confirm the in-frame sequence of the inserts. psflt-1* was generated by site directed mutagenesis (Stratagene) of 2278-AATGATTG-TACCACACAAAGT (SEQ ID NO:8) in psflt-1 to AAC-GACTGCACAACTCAGAGC (SEQ ID NO:9).

Deparaffinized sections were incubated with serum-free protein block (Dako or Biogenex). Endogenous peroxidase and alkaline phosphatase were quenched with $H_2O_2$ and levamisole (Vector Laboratories). Immunolocalization was performed with rabbit antibody against the unique carboxyl-terminus of sflt-1 (1:1000; Orecchia et al., J. Cell Sci. 116:3479, 2003), rabbit antibody against the unique carboxyl-terminus of mbflt-1 (1:1000; clone C-17, Santa Cruz Biotechnology), goat antibody against mouse VEGF-A (1:200; R&D Systems), goat antibody against human vascular cell adhesion molecule-1 (1:100; Santa Cruz Biotechnology), rabbit antibody against Cre recombinase (1:5,000; EMD/Novagen) using biotin-streptavidin-horseradish peroxidase, alkaline phosphatase, or immunofluorescent methods using FITC- and PE-conjugated secondary antibodies (Vector Laboratories). Counter-stain was obtained with Mayer's hematoxylin (Lillie's Modified, Dako), Nuclear FastRed (Vector Laboratories), or DAPI (1:25,000; Molecular Probes). Specificity was assessed by staining with control isotype non-immune IgG, omitting primary antibody, or pre-adsorbing the primary antibody with a ten-fold molar excess of the immunizing peptide.

In situ hybridization was carried out on formaldehyde fixed cryosections as previously described. Digoxigenin (DIG)-labeled sense and anti-sense riboprobes were transcribed from mouse sflt-1 and VEGF-A cDNAs using the DIG RNA-labeling kit (Boehringer-Mannheim). The sflt-1 probe corresponded to the divergence site of sflt-1 as previously reported 6. DIG-labeled probes were hybridized, slides were washed under high-stringency conditions, incubated with alkaline phosphatase-conjugated anti-DIG antibody (1:2000; Boehringer-Mannheim), and stained with NBT/BCIP (Boehringer-Mannheim).

Cell permeable enzymatically active Cre recombinase (NLS-Cre) or NLS-β-galactosidase (Harel et al., Mol. Biol. Cell. 14:4387, 2003), both containing a 6-His tag (SEQ ID NO: 15 and an SV40 derived nuclear localization signal, were dissolved in PBS (0.6 mg/ml) and dropped on to the surface of the cornea at the rate of 1 μl/min for 5 min.

Recombinant sflt-1/Fc or control isotype $IgG_1$-Fc were injected (5 μg/2 μl) into the corneas of fellow eyes of corn1 (at 2 and 3 weeks of age) and Pax6$^{+/-}$ (at 6 and 7 weeks of age) mice and morphometric measurements of vascularized area on corneal flat mounts were performed, as previously reported (Ambati et al., Invest. Ophthalmol. Vis. Sci. 44:590, 2003; Ambati et al., Cornea 22:465, 2003), at 4 (corn1) and 8 (Pax6$^{+/-}$) weeks of age.

Enzyme-linked immunosorbent assays (ELISAs) were used according to the manufacturer's instructions to quantify sflt-1 (Quantikine, R&D Systems) and free VEGF-A (RELIDA, RELIATech GmbH). Measurements were normalized to total protein (Bio-Rad). Immunoblotting was performed with rabbit antibody against the amino-terminus of flt-1 (1:1,000; Angiobio), rabbit antibodies against the unique carboxyl-terminus of sflt-1 (1:100 or 1:1,000), goat antibody against mouse VEGF-A (1:1,000; R&D Systems), rabbit antibody against mouse VEGFR-2 (1:1,000; clone T014), or rabbit antibody against Cre recombinase (1:10,000), and loading was assessed with rabbit antibody against human GAPDH (1:2,000; Abcam). Mouse cornea lysates were immunoprecipitated with goat antibody against mouse VEGF-A (2 μg/ml, R&D Systems) immobilized to protein G-agarose, subjected to SDS-PAGE, and immunoblotted with biotinylated goat antibody against the amino-terminus of mouse flt-1 (1:1,000, R&D Systems).

Total mouse cornea RNA was prepared (RNAqueous, Ambion) and cDNA was synthesized by reverse transcription (TaqMan, Applied Biosystems) and analyzed by real-time quantitative polymerase chain reaction (ABI 7000, Applied Biosystems). The primers for sflt-1 were: forward 5'-AGGT- GAGCACTGCGGCA-3' (SEQ ID NO:10), reverse 5'-ATGAGTCCTTTAATGTTTGAC-3' (SEQ ID NO:11). The primers for VEGF-A were described in Zhang et al (Biochem. Biophys. Res. Commun. 292:860, 2002). FAM (6-carboxyfluorescein)-labeled probes (Maxim Biotech) were used as target hybridization probes. sflt-1 and Vegfa expression were quantified and normalized to glyceraldehyde-3-phosphate dehydrogenase (Gapdh) or 18S rRNA levels by polymerase chain reaction with reverse transcription (RT-PCR) using TaqMan gene expression assays (Applied Biosystems).

Suspensions of cells isolated from mouse cornea by incubation with collagenase D (20 U/ml; Roche Diagnostics) and keratanase (5 U/ml; Sigma-Aldrich) treatment were incubated in Fc block (0.5 mg/ml; BD Pharmingen) for 15 min on ice. GFP expression was quantified using Alexa Fluor 488-conjugated rabbit antibody against GFP (1:500; Molecular Probes). Cells were stained after fixation with 4% paraformaldehyde and permeabilization with 1% Triton X-100 (Sigma Aldrich) and were subjected to FACS analysis (FACSCalibur, BD Biosciences). Monocytes/macrophages ($CD11b^+$ $CD115^+F4/80^+$) and neutrophils ($CD11b^+F4/80^-$ $Gr-1^+$), in cells isolated from cardiac blood after erythrocyte hemolysis with lysis buffer (eBioscience), were gated by FITC-conjugated rat antibody against mouse CD11b (1:100; eBioscience), RPE-Cy5-conjugated rat antibody against mouse F4/80 (1:10; Serotec), PE-conjugated rat antibody against mouse CD115 (1:1,000; eBioscience), and Alexa Fluor 647-conjugated rat antibody against mouse Gr-1 (1:100; eBioscience).

Cultured mouse corneal epithelial cells were maintained in EMEM supplemented with 10% FCS, 1% glutamine, and antibiotics at 37° C. under 5% $CO_2$. Secreted sflt-1 levels in the supernatant were measured by ELISA (R&D Systems) at 0, 8 and 24 h after serum starvation.

Differences in incidence of CV and mean levels of protein, mRNA, and CV area were compared with two-tailed Fisher's exact test and Mann Whitney U test with Bonferroni correction for multiple comparisons, respectively. P values<0.05 were considered significant. Data are presented as mean±s.e.m.

As previously noted, specificity of sflt-1 immunolocalization in mouse cornea was inhibited by the immunizing peptide but not by an unrelated, negative-control peptide. No staining was observed when anti-sflt-1 antibody was replaced with isotype control IgG or when it was omitted.

Additional studies showed that sflt-1 was present extracellularly in vivo and in vitro. The pattern of sflt-1 immunostaining is diffuse and extends beyond cell borders in the superficial layers of mouse corneal epithelium, and appears external to cytoplasm and in intercellular spaces in the deeper layers. Data generated from ELISA experiments demonstrated that mouse corneal epithelial cells constitutively secrete sflt-1.

Further, VEGF-A produced by the cornea colocalized with sflt-1 because immunoreactivities of sflt-1 and VEGF-A were identified as colocalizing in the mouse cornea. Moreover, neutralizing flt-1 protein was capable of abolishing corneal avascularity. Corneal injection of anti-flt-1 neutralizing antibody (nAb) but not isotype control IgG injection elicits invasion of $CD31^+$ LYVE-1-blood vessels into cornea of mice 14 days after injection. Western blots subsequently showed a shift in VEGF-A from bound to free form.

In addition, neutralizing flt-1 gene expression abolished corneal avascularity. pCre but not pNull induces corneal vascularization in flt-$1^{loxP/loxP}$ mice. After injection, Cre is expressed and sflt-1 expression is reduced compared to pNull injection.

Further, the corneal vascularization induced by sflt-1 shRNA was not due to inflammation. Mice eyes were systemically depleted of monocytes/macrophages and neutrophils by injection of clodronate liposomes and anti-Gr-1 antibody. Flow cytometry reveals the monocyte/macrophage and neutrophil fractions of peripheral blood leukocytes, normalized to control levels, were markedly suppressed by clodronate liposomes and anti-Gr-1 antibody injection compared to controls (PBS-liposomes and non-immune rat IgG, respectively) 3 days after initial injection. *P<0.05 compared to controls. In addition, pshRNA-sflt-1 did not elevate VEGF-A mRNA levels compared to pshRNA-mbflt-1 or control uninjected corneas. Individual VEGF-A isoform levels measured by real time RT-PCR 2 days after injection were divided by GAPDH levels and normalized to control levels. No pairwise differences were statistically significant by Bonferroni corrected Mann Whitney U test.

The present data indicate that corneal vascularization induced by sflt-1 shRNA was specifically due to mRNA knockdown because $p_2$shRNA-sflt-1, targeted against a different sequence than by pshRNA-sflt-1, also induced corneal vascularization. In addition, the present data indicate that exogenous VEGF-A induces corneal vascularization by overwhelming endogenous sflt-1. Recombinant mouse VEGF-A164 injection induces CV in a dose-dependent manner and is blocked by co-administration (5 μg) of recombinant sflt-1/Fc but not isotype control IgG1-Fc.

The present studies further found that mbflt-1 expressed in the Manatee cornea was inhibited by the immunizing peptide but not by an unrelated, negative-control peptide.

In addition, naked plasmids are able to transfect mouse corneas in vivo. Flow cytometry data reveal that greater than 70% of corneal cells express GFP 1 day after injection of pGFP as compared to pNull.

SiRNA Design and Synthesis: siRNAs against sFLT unique sequence (differences in bold; 3rd sequence is identical):

| Human | SEQ ID NO: | Mouse | SEQ ID NO: |
|---|---|---|---|
| AAAGGCTGTTTTCTCTCGGAT | 4 | AAAGGCCATTTTCTCTCGGAT | 6 |
| AAAAGCACAAGGAATGATTGT | 5 | AAAAGCAGGAGGAATGATTGT | 7 |
| AATGATTGTACCACACAAAGT | 2 | AATGATTGTACCACACAAAGT | 2 |

Provided herein are unique homologous siRNA against the C-terminal tail of sVEGFR 1 that suppress its secretion in vitro. HUVEC cells at 50% confluency were transfected with siRNAs against sVEGFR 1 (3 separate sequences, with high homology for mouse and human sVEGFR 1 targeting the unique C-terminal sequence) and an siRNA against GADPH and incubated for 5 days. Culture medium was collected at 1, 3, and 5 days for sVEGFR 1 expression assay by ELISA (R&D). siRNA-sVEGFR 1 sequence (SEQ ID NO:2) suppressed the regular increase in sVEGFR 1 expression by 64.0% over 5 days.

Figure 3:
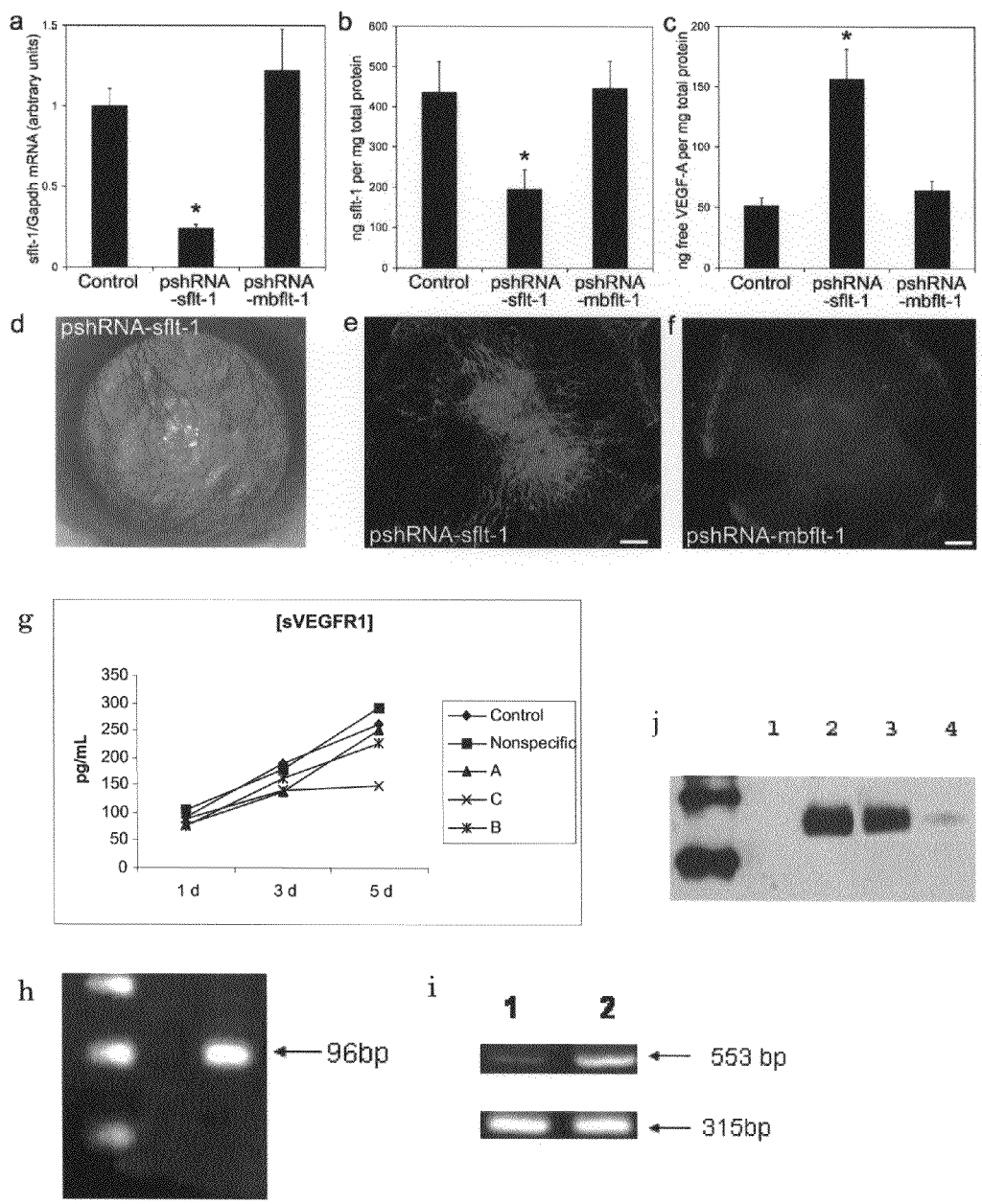
FIG. 3, panel A is a bar graph indicating that sflt-1 mRNA knockdown abolishes corneal avascularity. Real time RT-PCR reveals reduced sflt-1 mRNA in wild-type mouse corneas 3 days after injection of pshRNA-sflt-1 but not pshRNA-mbflt-1. * $P<0.05$, Bonferroni corrected Mann Whitney U test. Error bars depict s.e.m.

As shown in FIG. 3, panel G, expression of sVEGR 1 is decreased by siRNA sequence provided in SEQ ID NO:2. Intracorneal delivery of this siRNA down-regulates unique C-terminal sequence and VEGF-binding domains of sVEGFR-1. Intrastromal delivery of plasmid expressing siRNA against the uniquely identical target sequence of mouse and human sVEGFR 1 into the cornea knocks down expression of the unique c-terminal 96 nucleotide sequence of sVEGFR 1 within 2 days. Further, expression of domains 2-3, the VEGF-binding domains of sVEGFR 1 is also knocked down. FIG. 3, panel H shows suppression of unique tail of sFLT by siRNA targeting (middle lane). FIG. 3, panel I shows suppression of mRNA of VEGF binding domains (553 bp) of sFLT by siRNA targeting unique tail. Expression of 18sRNA control (315 bp) is unaffected. Further, FIG. 3, panel J shows that siRNA-sFLT decreases VEGF bound to sFLT and increases free VEGF in cornea. Mouse corneas were subjected to immunoprecipitation by antibody to sFLT unique tail, then underwent Western blot for VEGF (band visible at 25 kD). Lanes 1 and 2 are control mouse cornea: 1 is supernatant fraction, 2 is immunoprecipitate. Lanes 3 and 4 are from mouse corneas treated with siRNA-sFLT: 3 is supernatant; 4 is immunoprecipitate. These data demonstrate that siRNA knocking down sFLT frees VEGF from sFLT sequestration.

The inventors have also demonstrated that, while siRNA-sFLT breaches corneal avascularity, it can be restored by co-delivery of translationally silent mutant of sVEGFR 1. Intrastromal delivery of plasmid expressing siRNA against the uniquely identical target sequence of mouse and human sVEGFR-1 into the cornea knocks down sVEGFR 1 expression within 2 days and stimulates blood vessel formation into the cornea that is spatially correlated with the injection track.

In addition, mouse corneas 14 days post-injection with pSEC-siRNA-sVEGFR1 (SEQ ID NO:2) show neovascularization spatially correlated with the injection track. Further, generation of translationally silent mutant of sVEGFR 1 was performed by substituting nucleotides 61-81 of this 96 nucleotide sequence (or 2278-2298 of the sFLT gene (sFLT=1st 6 domains of FLT+unique tail in lieu of domain 7 of FLT) which normally codes for: AAT GAT TGT ACC ACA CAA AGT (SEQ ID NO: 2) (amino acids=NDCTTQS; SEQ ID NO: 12). The alternate (mutant) sequence to be substituted for this is: AAC GAC TGC ACA ACT CAG AGC (SEQ ID NO: 9). Cotransfection of plasmid expressing this mutant sFLT along with a plasmid expressing siRNA against normal sFLT resulted in restoration of corneal sFLT expression and normal corneal avascularity. Moreover, co-injection of plasmids expressing siRNA-sFLT and translationally silent mutant of sFLT theoretically resistant to that siRNA shows expression of unique tail of sFLT at 2 days after injection.

The present studies have determined that sVEGFR 1 is highly expressed in normal human and mouse corneal epithelium and to a lesser degree in corneal keratocytes, and that there is a preferential gradient of sVEGFR 1 in peripheral limbal cornea relative to sclera which would theoretically contribute to the limbal avascular barrier. Further, the present data indicates that sVEGFR 1 and VEGF which is normally bound to sVEGFR 1 is decreased in neovascularized human corneas thus identifying sVEGFR 1 as a mediator of corneal avascularity.

Accordingly, provided herein are a series of nucleic acid molecules developed to down-regulate expression of sVEGFR 1 by nucleic acid interference. The unique C-terminal tail of sVEGFR 1 was specifically targeted using a target sequence that is uniquely identical in the mouse and human gene. Transcriptional disruption of this tail also down-regulates the mRNA transcript of domains 2-3 of sVEGFR 1, its VEGF-binding domains, demonstrating knockdown of this gene. Delivery of a naked plasmid into the mouse cornea breaches corneal avascularity. This effect is reversed by delivery of a plasmid expressing a translationally silent mutant of sVEGFR 1. Further, corneal avascularity was not affected by an siRNA which down-regulates pigment epithelial derived factor.

The selection process for siRNA screening relied on homology of target sequence between the mouse and human VEGF gene because such homology reflects evolutionary conservation which in turn likely indicates a target of import.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a condition associated with decreased vascularity in a subject, the method comprising administering to a subject in need thereof having the condition associated with decreased vascularity a compound that increases the bioavailability or biological activity of VEGF by reducing the bioavailability or biological activity of a VEGF inactivating agent, and wherein the administering is sufficient to treat the condition in the subject by increasing vascularity, wherein the condition is selected from the group consisting of preeclampsia, systemic hypertension, cerebrovascular disorders, cardiovascular disorders, peripheral vascular disease, vascular regeneration/recovery, and wound healing disorders and wherein the VEGF inactivating agent is fms-like tyrosine kinase is soluble flt-1 (sflt-1) or membrane bound flt-1 (mbflt-1), and wherein the compound is a nucleic acid molecule.

2. The method of claim 1, wherein the VEGF is selected from the group consisting of VEGF-A, VEGF-B, VEGF-C and VEGF-D.

3. The method of claim 1, wherein the compound comprises a double stranded nucleic acid molecule having one strand that is at least 95% complementary to at least a portion of a nucleic acid sequence encoding the agent.

4. The method of claim 3, wherein the nucleic acid molecule comprises an interfering RNA molecule.

5. The method of claim 4, wherein the interfering RNA molecule is selected from the group consisting of shRNA, siRNA and miRNA.

6. The method of claim 4, wherein the interfering RNA is 10 to 40 nucleotides in length.

7. The method of claim 1, wherein the expression of the agent is reduced by an inducible excision system.

8. The method of claim 7 wherein the inducible excision system is cre-lox or FLP/FRT excision system.

9. The method of claim 7, wherein excision is facilitated by the introduction of exogenous CRE recombinase.

10. The method of claim 9, wherein the introduction is by the topical application of NLS-Cre.

11. The method of claim 1, wherein the compound is administered via a topical, intravenous, oral, or intracanalicular route.

12. The method of claim 1 wherein the condition is preeclampsia.

13. A method of treating preeclampsia in a subject, the method comprising administering to a subject in need thereof a compound that increases the bioavailability or biological activity of VEGF by reducing the bioavailability or biological activity of a VEGF inactivating agent, wherein the VEGF inactivating agent is fms-like tyrosine kinase is soluble flt-1 (sflt-1) or membrane bound flt-1 (mbflt-1), wherein the compound is a nucleic acid molecule and wherein the nucleic acid molecule is administered in an amount that is sufficient to increase vascularity in the subject.

* * * * *